United States Patent
Byun et al.

(10) Patent No.: US 10,202,459 B2
(45) Date of Patent: Feb. 12, 2019

(54) METHODS OF INHIBITING PATHOLOGICAL ANGIOGENESIS WITH DOPPEL-TARGETING MOLECULES

(71) Applicants: SEOUL NATIONAL UNIVERSITY R&DB FOUNDATION, Seoul (KR); UNIVERSITY OF ULSAN, Ulsan (KR); KOREA INSTITUTE OF SCIENCE AND TECHNOLOGY, Seoul (KR); PHAROSGEN, Seoul (KR)

(72) Inventors: Youngro Byun, Seoul (KR); In San Kim, Daegu (KR); Ahmed Al-Hilal Taslim, Seoul (KR); Sang-Yoon Kim, Seoul (KR); Ye Ji Jang, Seoul (KR)

(73) Assignees: SEOUL NATIONAL UNIVERSITY R&DB FOUNDATION, Seoul (KR); UNIVERSITY OF ULSAN, Ulsan (KR); KOREA INSTITUTE OF SCIENCE AND TECHNOLOGY, Seoul (KR); PHAROSGEN, Seoul (KR)

( * ) Notice: Subject to any disclaimer, the term of this patent is extended or adjusted under 35 U.S.C. 154(b) by 0 days.

(21) Appl. No.: 15/363,103

(22) Filed: Nov. 29, 2016

(65) Prior Publication Data

US 2017/0183416 A1 Jun. 29, 2017

(30) Foreign Application Priority Data

Nov. 30, 2015 (KR) .................. 10-2015-0168485

(51) Int. Cl.
| | | |
|---|---|---|
| *A61K 39/395* | (2006.01) | |
| *C07K 16/18* | (2006.01) | |
| *C07K 16/28* | (2006.01) | |
| *A61K 31/727* | (2006.01) | |
| *G01N 33/574* | (2006.01) | |
| *G01N 33/68* | (2006.01) | |
| *C07K 14/705* | (2006.01) | |
| *C12N 15/113* | (2010.01) | |
| *A61K 47/54* | (2017.01) | |

(52) U.S. Cl.
CPC ........ *C07K 16/2872* (2013.01); *A61K 31/727* (2013.01); *A61K 47/554* (2017.08); *C07K 14/705* (2013.01); *C07K 16/28* (2013.01); *C12N 15/113* (2013.01); *G01N 33/57492* (2013.01); *G01N 33/6893* (2013.01); *A61K 39/3955* (2013.01); *C07K 16/18* (2013.01); *C07K 2317/14* (2013.01); *C07K 2317/73* (2013.01); *C07K 2317/76* (2013.01); *C12N 2310/11* (2013.01); *C12N 2310/3515* (2013.01); *G01N 2333/705* (2013.01)

(58) Field of Classification Search
None
See application file for complete search history.

(56) References Cited

U.S. PATENT DOCUMENTS

2010/0028256 A1* 2/2010 St. Croix ............ C12Q 1/6886
424/1.49
2017/0260278 A1 9/2017 Byun et al.

OTHER PUBLICATIONS

Al-Hilal et al., "Targeting prion-like protein doppel selectively suppresses tumor angiogenesis," The Journal of Clinical Investigation, vol. 126, No. 4, pp. 1251-1266, Apr. 2016.
Al-Hilal et al., "Abstract 3277: Prion-like protein "Doppel" is a selective therapeutic target for tumoral angiogenesis," Proceedings of the 107th Annual Meeting of the American Association for Cancer Research [Abstract] (Jul. 2016) vol. 76, Issue 14 Supplement.
Office Action dated Apr. 26, 2018 in U.S. Appl. No. 15/450,272 (US 2017-0260278).

* cited by examiner

*Primary Examiner* — Marianne P Allen
(74) *Attorney, Agent, or Firm* — Foley & Lardner LLP

(57) ABSTRACT

Described herein are doppel-targeting molecules useful for inhibiting pathological angiogenesis and treating diseases and conditions associated with pathological angiogenesis, such as tumors, cancers, atherosclerosis, tuberculosis, asthma, pulmonary arterial hypertension (PAH), neoplasms and neoplasm-related conditions, and for detecting doppel expression in a subject. Related compositions and methods also are described.

14 Claims, 30 Drawing Sheets

Specification includes a Sequence Listing.

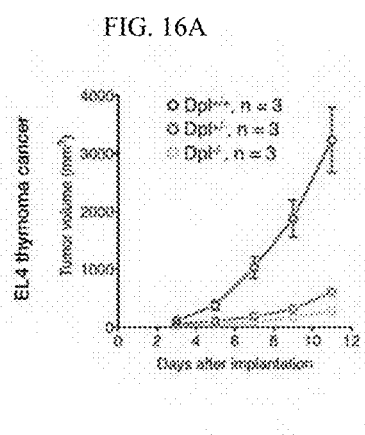
FIG. 16A
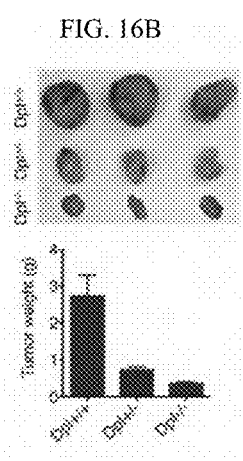
FIG. 16B
FIG. 16C
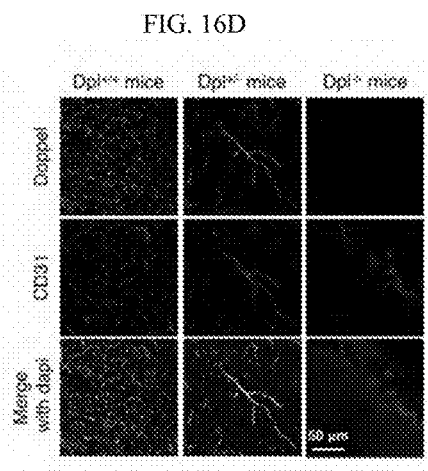
FIG. 16D

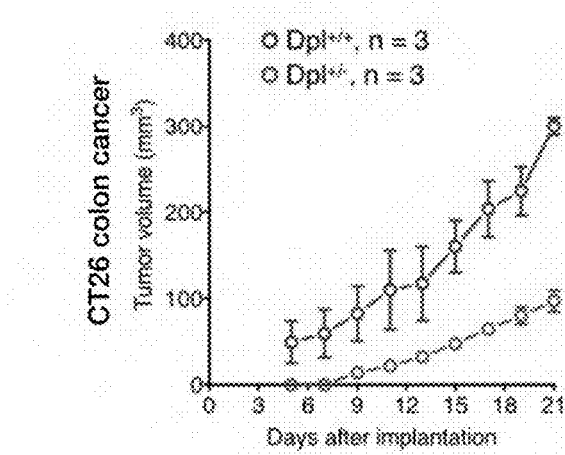
FIG. 17A
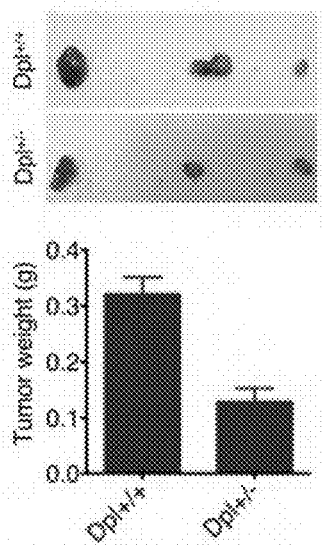
FIG. 17B
FIG. 17C
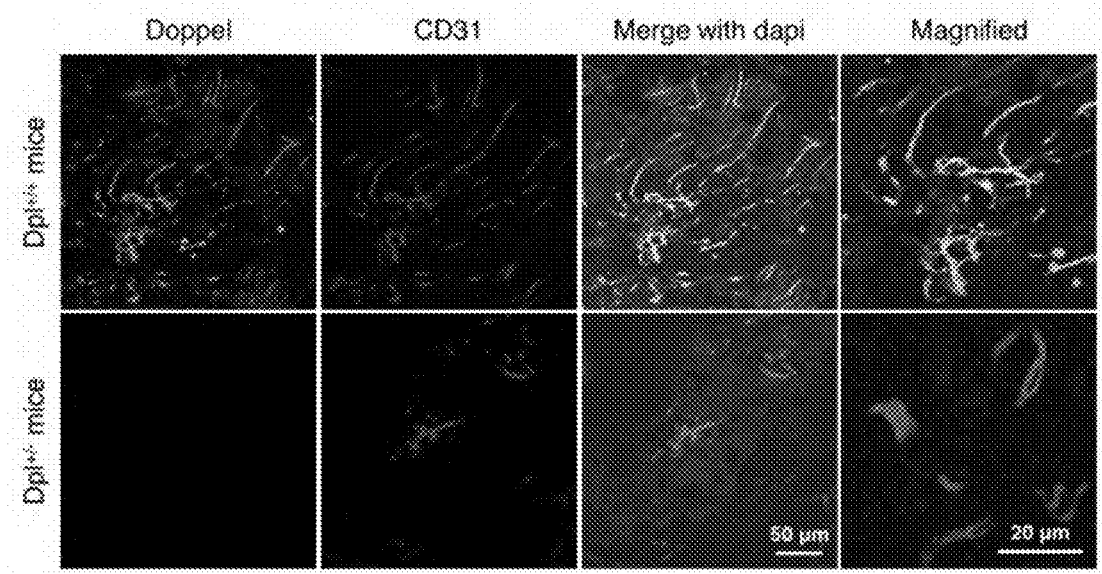
FIG. 17D

FIG. 18A
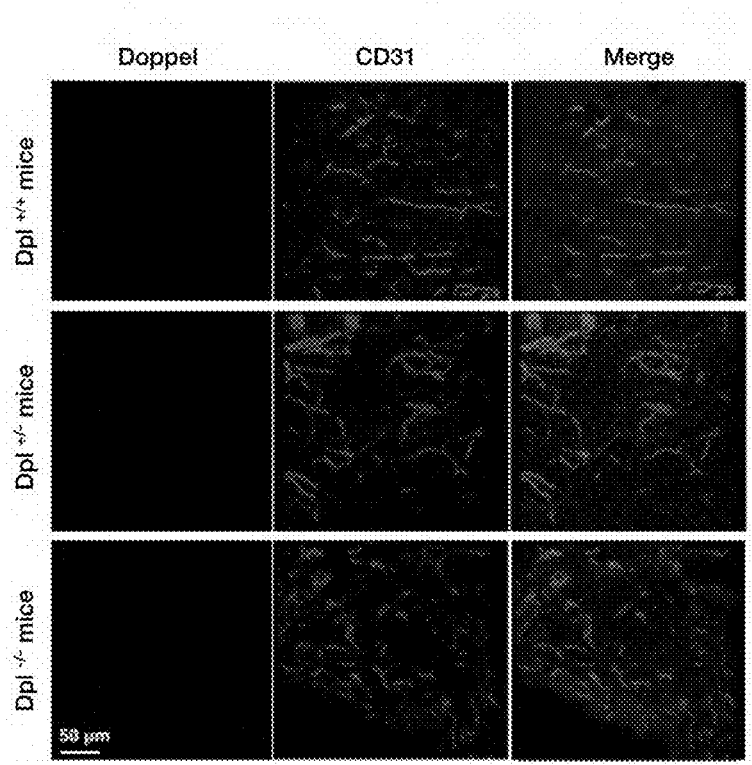
FIG. 18B 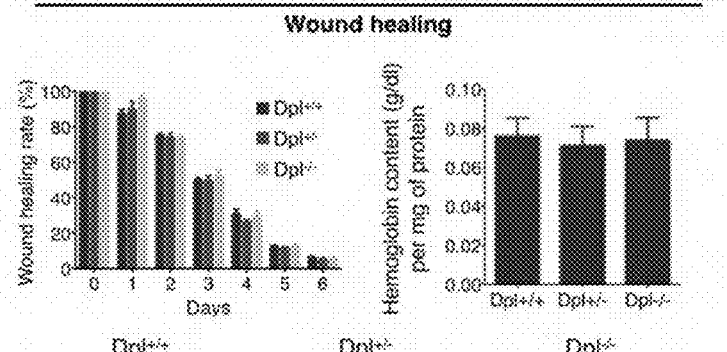 FIG. 18C
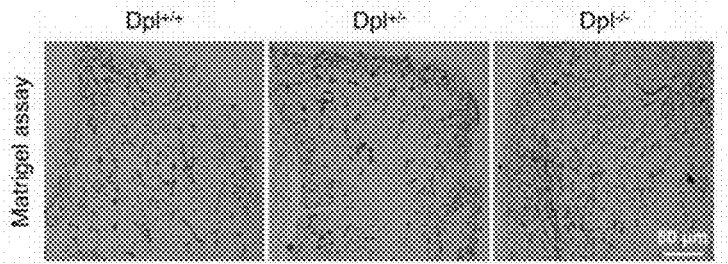
FIG. 18D

FIG. 19A 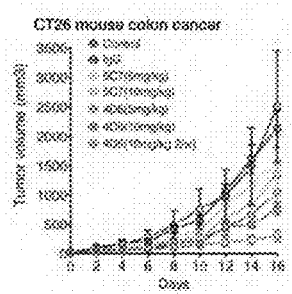 FIG. 19B 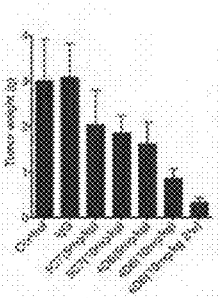 FIG. 19C 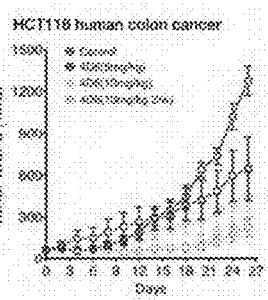 FIG. 19D 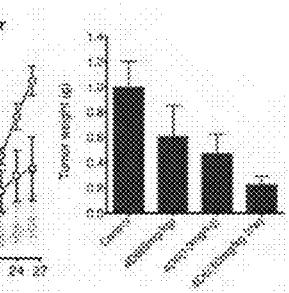
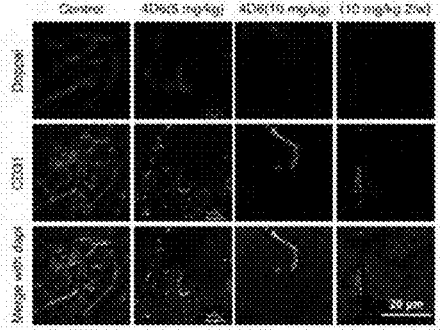 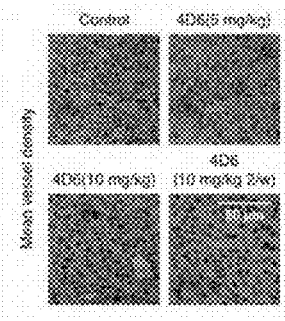 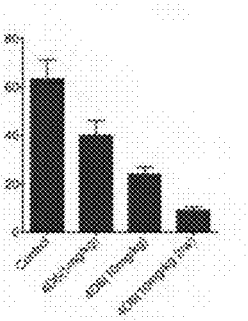
FIG. 19E  FIG. 19F  FIG. 19G FIG. 20A
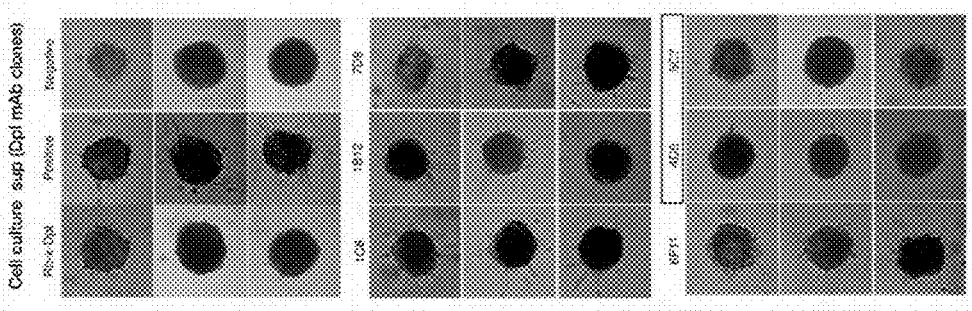
FIG. 20C
FIG. 20B
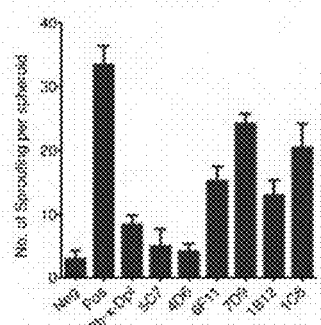
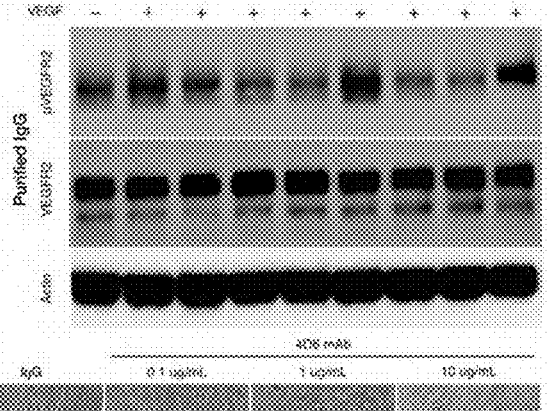
FIG. 20D FIG. 21A
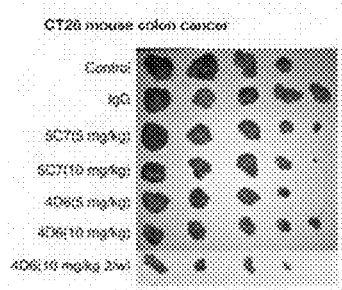
FIG. 21B
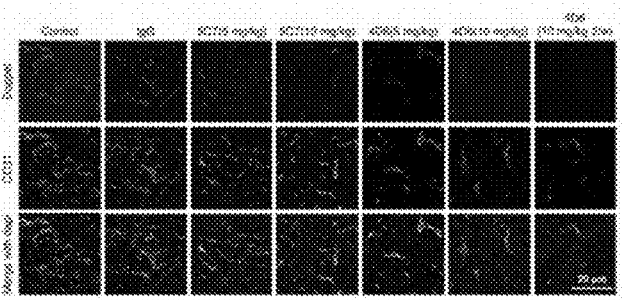
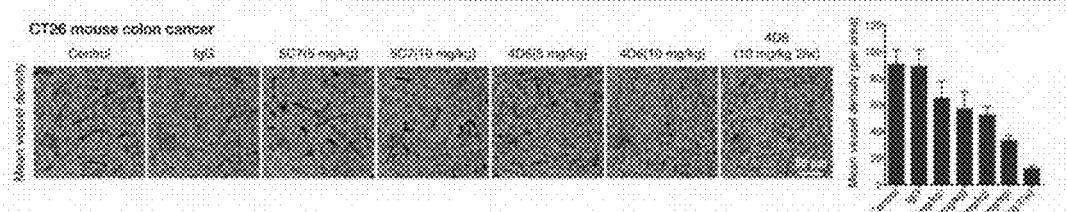
FIG. 21C
FIG. 21D

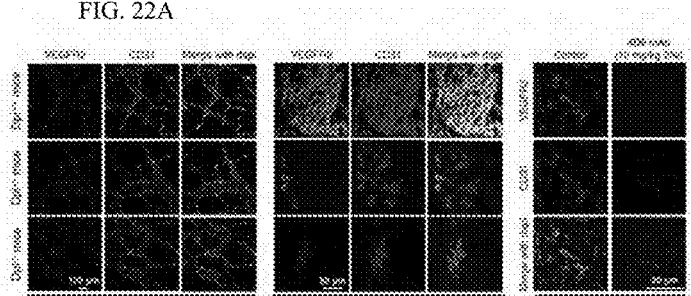
FIG. 22A  FIG. 22B
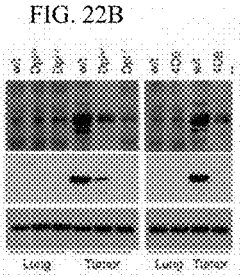
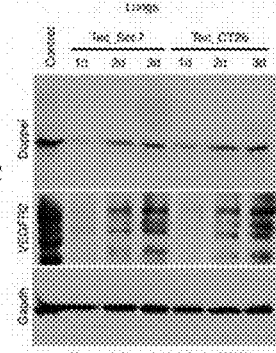
FIG. 22C
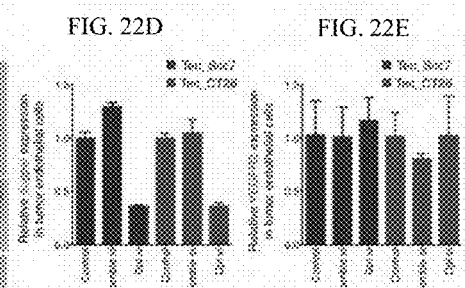
FIG. 22D  FIG. 22E
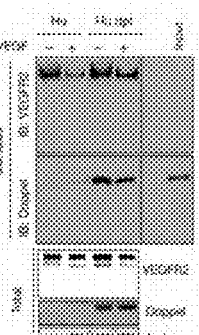
FIG. 22F
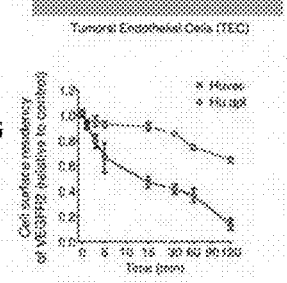
FIG. 22G
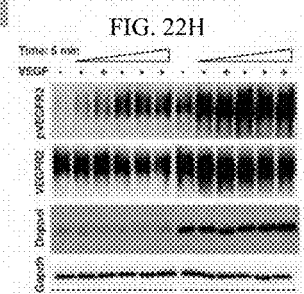
FIG. 22H
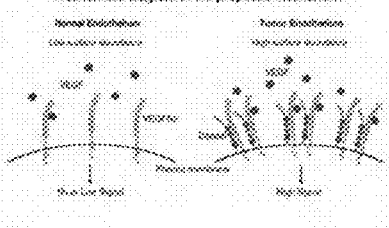
FIG. 22I FIG. 27A
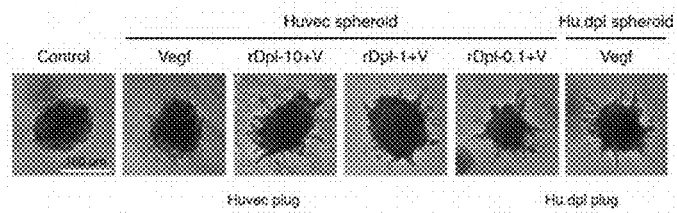
FIG. 27B
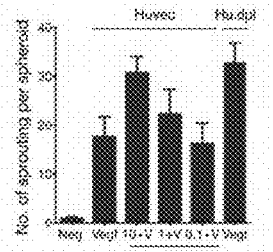
FIG. 27C
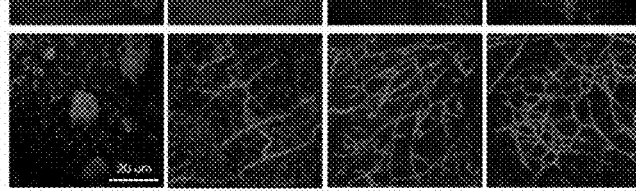
FIG. 27D
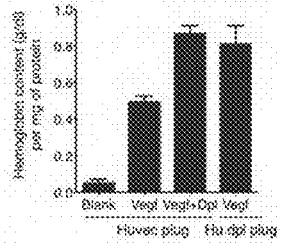
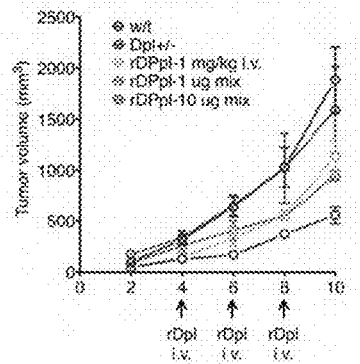
FIG. 27E
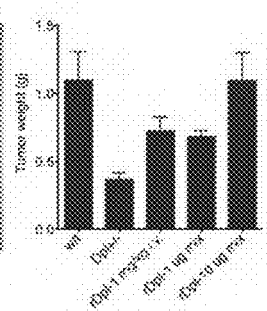
FIG. 27F
FIG. 27G

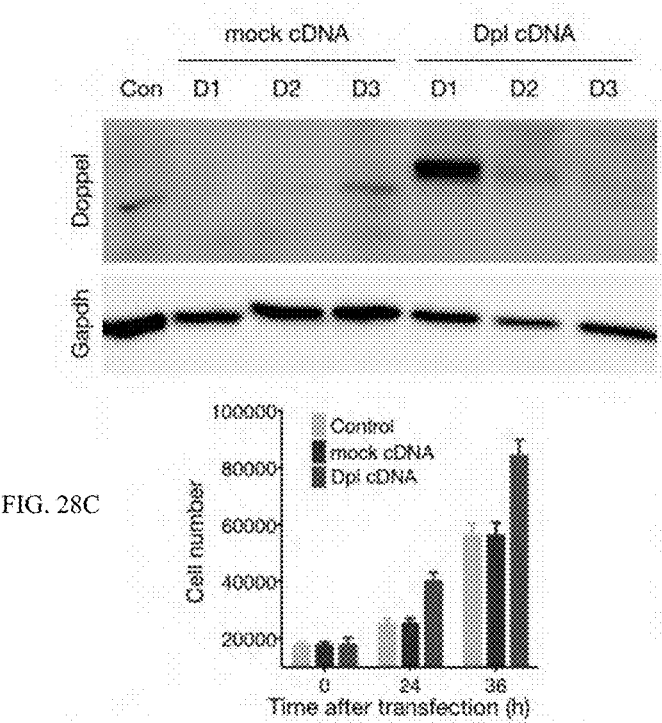
FIG. 28A
FIG. 28B
FIG. 28C
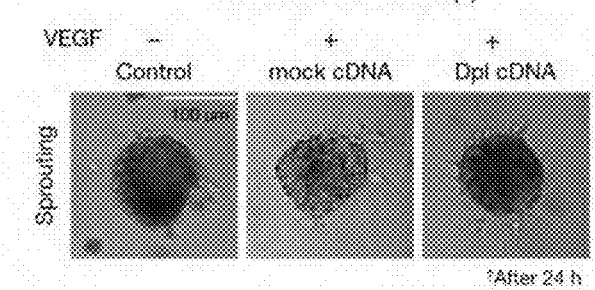
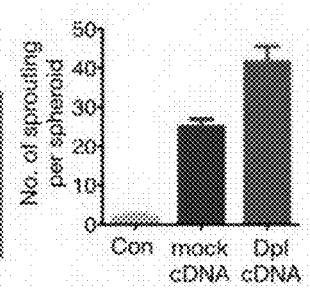
FIG. 28D
FIG. 28E FIG. 30A
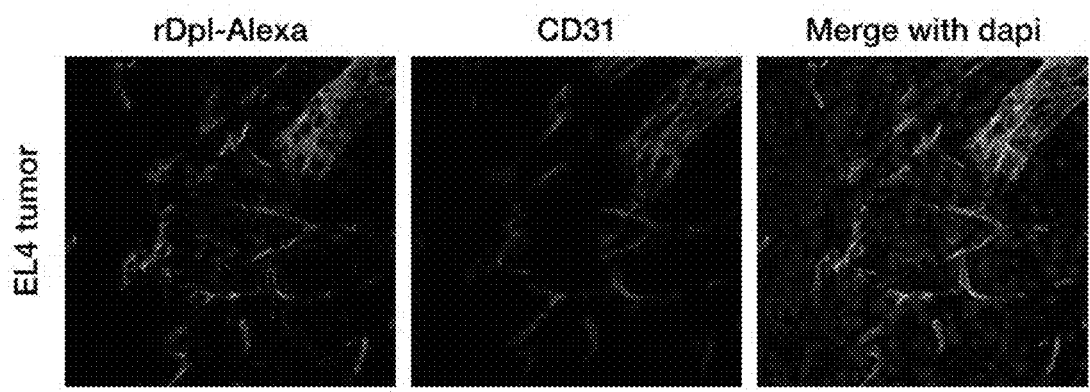
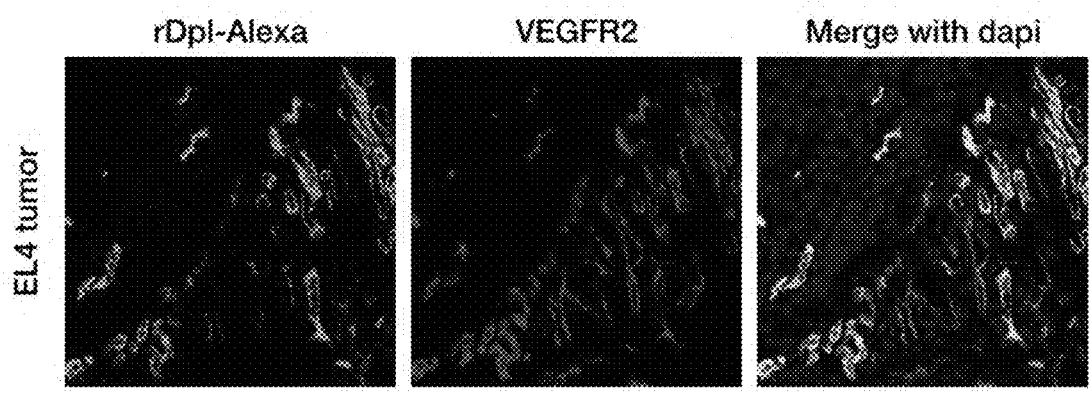
FIG. 30B

METHODS OF INHIBITING PATHOLOGICAL ANGIOGENESIS WITH DOPPEL-TARGETING MOLECULES

CROSS-REFERENCE TO RELATED APPLICATIONS

This application claims priority to South Korean Application 10-2015-0168485 filed Nov. 30, 2015, the entire contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Feb. 22, 2017, is named 109707-0106_SL.txt and is 2,220 bytes in size.

BACKGROUND

Cancer is a diverse set of diseases with vastly different genotypes and phenotypes. Nevertheless, angiogenesis (the formation of new blood vessels) plays an important role in the proliferation of cancer cells across cancer types. Indeed, the dependency of solid tumors on the growth of new blood vessels has made tumor blood vessels an appealing target for cancer therapy. Thus, cancer therapies that interfere with angiogenesis are being developed. For example, bevacizumab, a humanized monoclonal antibody against the vascular endothelial growth factor (VEGF), has been used to potentiate the effects of different active chemotherapeutic regimens.

To date, various agents that inhibit angiogenesis (e.g., endostatin, angiostatin, and thrombospondin) have been described. However, angiogenesis is important to normal physiological processes, such as growth and development or wound healing. Thus, current anti-angiogenesis therapies that do not discriminate between normal versus pathological angiogenesis, such as anti-VEGF monoclonal antibodies and tyrosine kinase receptor (TKR, also known as receptor tyrosine kinase (TKR)) inhibitors, suppress beneficial as well as pathological angiogenesis, by inducing systemic depression of cell signaling. For example, considering the vast biological role of VEGF in thyroid function, bone marrow function, immunomodulation, kidney function, vascular homeostasis, coagulation initiation, and physiological angiogenesis, the systematic suppression of VEGF can interfere will all of these essential functions.

Thus, there is a need for anti-angiogenesis therapies that discriminate between normal versus pathological angiogenesis.

SUMMARY

Described herein are doppel-targeting molecules for use in inhibiting pathological angiogenesis in a subject in need thereof, or for use in treating a tumor in a subject in need thereof, inhibiting tumorigenesis in a subject in need thereof, decreasing the vasculature of a tumor in a subject in need thereof, treating a disease or condition selected from cancer, atherosclerosis, tuberculosis, asthma, and pulmonary arterial hypertension (PAH) in a subject in need thereof, or for treating a neoplasm or neoplasm-related condition, such as breast carcinoma, lung carcinoma, gastric carcinoma, esophageal carcinoma, colorectal carcinoma, liver carcinoma, ovarian carcinoma, arrhenoblastoma, cervical carcinoma, endometrial carcinoma, endometrial hyperplasia, endometriosis, fibrosarcoma, choriocarcinoma, head and neck cancer, nasopharyngeal carcinoma, laryngeal carcinoma, hepatoblastoma, Kaposi's sarcoma, melanoma, skin carcinoma, hemangioma, cavernous hemangioma, hemangioblastoma, pancreas carcinoma, retinoblastoma, astrocytoma, glioblastoma, Schwannoma, oligodendroglioma, medulloblastoma, neuroblastoma, rhabdomyosarcoma, osteogenic sarcoma, leiomyosarcoma, urinary tract carcinoma, thyroid carcinoma, Wilm's tumor, renal cell carcinoma, prostate carcinoma, abnormal vascular proliferation associated with phakomatoses, edema associated with a brain tumor, and/or Meigs' syndrome, or for use in detecting doppel expression in a subject.

In some embodiments, the doppel-targeting molecules binds to doppel and inhibits doppel-tyrosine kinase receptor signaling, such as inhibiting or interfering with the interaction between doppel and a tyrosine kinase receptor selected from VEGFR2, VEGFR1, VEGFR3, bFGFR, and PDGFR.

In some embodiments, the doppel-targeting molecule is selected from an anti-doppel antibody, a doppel-binding fragment of an anti-doppel antibody, and a heparin-containing conjugate.

In some embodiments, the doppel-targeting molecule is an anti-doppel antibody selected from
(i) an antibody produced by hybridoma cell line clone 4D6 or a doppel-binding fragment or derivative thereof;
(ii) an antibody produced by hybridoma cell line clone 5C7 or a doppel-binding fragment or derivative thereof
(iii) an antibody produced by hybridoma cell line clone 7D9 or a doppel-binding fragment or derivative thereof;
(iv) an antibody produced by hybridoma cell line clone 1B12 or a doppel-binding fragment or derivative thereof;
(v) an antibody produced by hybridoma cell line clone 1C8 or a doppel-binding fragment or derivative thereof; and
(vi) an antibody produced by hybridoma cell line clone 6F11 or a doppel-binding fragment or derivative thereof.

In some embodiments, the doppel-targeting molecule is a heparin-containing conjugate comprising a heparin moiety conjugated to a bile acid moiety or a sterol moiety. In some embodiments, the doppel-targeting molecule is a LMWH-oligoDOCA conjugate. In some embodiments, the doppel-targeting molecule is a LMWH-oligoDOCA conjugate selected from LHbisD4, LHmonoD1, LHmonoD2, LHmonoD4, LHbisD1, LHbisD2, LHtriD1, LHtriD3, and LHtetraD1.

In some embodiments, the doppel-targeting molecule is formulated for intravenous injection, oral administration, subcutaneous injection, intraocular injection, intradermal injection, intramuscular injection, intraperitoneal injection, intratracheal administration, inhalation, intranasal administration, sublingual administration, buccal administration, rectal administration, vaginal administration, or topical administration.

In some embodiments, the doppel-targeting molecule is formulated in a composition for intravenous administration.

In some embodiments, the doppel-targeting molecule is formulated in a composition for oral administration. In some embodiments, the doppel-targeting molecule is formulated in a composition for oral administration. and selective absorption in the intestines or ileum.

Also described herein are methods of inhibiting pathological angiogenesis in a subject in need thereof, treating a tumor in a subject in need thereof, inhibiting tumorigenesis in a subject in need thereof, decreasing the vasculature of a tumor in a subject in need thereof, treating a disease or condition selected from cancer, atherosclerosis, tuberculosis, asthma, and pulmonary arterial hypertension (PAH) in a subject in need thereof, treating a neoplasm or neoplasm-related condition in a subject in need thereof, such as breast carcinoma, lung carcinoma, gastric carcinoma, esophageal carcinoma, colorectal carcinoma, liver carcinoma, ovarian carcinoma, arrhenoblastoma, cervical carcinoma, endometrial carcinoma, endometrial hyperplasia, endometriosis, fibrosarcoma, choriocarcinoma, head and neck cancer, nasopharyngeal carcinoma, laryngeal carcinoma, hepatoblastoma, Kaposi's sarcoma, melanoma, skin carcinoma, hemangioma, cavernous hemangioma, hemangioblastoma, pancreas carcinoma, retinoblastoma, astrocytoma, glioblastoma, Schwannoma, oligodendroglioma, medulloblastoma, neuroblastoma, rhabdomyosarcoma, osteogenic sarcoma, leiomyosarcoma, urinary tract carcinoma, thyroid carcinoma, Wilm's tumor, renal cell carcinoma, prostate carcinoma, abnormal vascular proliferation associated with phakomatoses, edema associated with a brain tumor, and/or Meigs' syndrome, and/or detecting doppel expression in a subject, wherein the methods comprise administering to the subject an effective amount of a doppel-targeting molecule as described herein.

In some embodiments, the doppel-targeting molecule is administered by oral administration, intravenous injection, subcutaneous injection, intraocular injection, intradermal injection, intramuscular injection, intraperitoneal injection, intratracheal administration, inhalation, intranasal administration, sublingual administration, buccal administration, rectal administration, vaginal administration, or topical administration. In some embodiments, the method comprises orally administering the doppel-targeting molecule. In some embodiments, the method comprises administering the doppel-targeting molecule by intravenous injection.

In accordance with any embodiments, the subject may be a human. In accordance with any embodiments, the subject may suffer from or be at risk of developing a tumor, a disease or condition selected from cancer, atherosclerosis, tuberculosis, asthma, and pulmonary arterial hypertension (PAH), or a neoplasm or neoplasm-related condition, such as breast carcinoma, lung carcinoma, gastric carcinoma, esophageal carcinoma, colorectal carcinoma, liver carcinoma, ovarian carcinoma, arrhenoblastoma, cervical carcinoma, endometrial carcinoma, endometrial hyperplasia, endometriosis, fibrosarcoma, choriocarcinoma, head and neck cancer, nasopharyngeal carcinoma, laryngeal carcinoma, hepatoblastoma, Kaposi's sarcoma, melanoma, skin carcinoma, hemangioma, cavernous hemangioma, hemangioblastoma, pancreas carcinoma, retinoblastoma, astrocytoma, glioblastoma, Schwannoma, oligodendroglioma, medulloblastoma, neuroblastoma, rhabdomyosarcoma, osteogenic sarcoma, leiomyosarcoma, urinary tract carcinoma, thyroid carcinoma, Wilm's tumor, renal cell carcinoma, prostate carcinoma, abnormal vascular proliferation associated with phakomatoses, edema associated with a brain tumor, and/or Meigs' syndrome.

In some embodiments, the doppel-targeting molecule is used or administered in an effective amount that is effective to interfere with the interaction of doppel and a tyrosine kinase receptor, such as VEGFR2, VEGFR1, VEGFR3, bFGFR, and/or PDGFR. In some embodiments, the effective amount is effective to inhibit angiogenesis. In some embodiments, the effective amount is effective to inhibit tumorigenesis. In some embodiments, the effective amount is effective to decrease the vasculature of a tumor. In some embodiments, the effective amount is effective to decrease pathological vasculature associated with cancer, atherosclerosis, tuberculosis, asthma, or pulmonary arterial hypertension (PAH), respectively.

With regard to methods and uses for detecting doppel expression in a subject, the doppel-targeting molecule may be administered to the subject or to a physiological sample obtained from the subject. The subject may be any described above, such as being at risk of developing a tumor, at risk of developing a disease or condition selected from cancer, atherosclerosis, tuberculosis, asthma, and pulmonary arterial hypertension (PAH), and/or at risk of developing a neoplasm or neoplasm-related condition, as described above.

Also provided are hybridoma cell lines that produce doppel-binding antibodies as described herein, including:
(i) hybridoma cell line clone 4D6 deposited on Nov. 23, 2016 with Korean Cell Line Research Foundation as mPrnd#4D6 under Accession Number KCLRE-BP-00384;
(ii) hybridoma cell line clone 5C7 deposited on Nov. 23, 2016 with Korean Cell Line Research Foundation as mPrnd#5C7 under Accession Number KCLRE-BP-00385;
(iii) hybridoma cell line clone 7D9 deposited on Nov. 23, 2016 with Korean Cell Line Research Foundation as mPrnd#7D9 under Accession Number KCLRE-BP-00387;
(iv) hybridoma cell line clone 1B12 deposited on Nov. 23, 2016 with Korean Cell Line Research Foundation as mPrnd#1B12 under Accession Number KCLRE-BP-00383;
(v) hybridoma cell line clone 1C8 deposited on Nov. 23, 2016 with Korean Cell Line Research Foundation as mPrnd#1C8 under Accession Number KCLRE-BP-00382; and
(vi) hybridoma cell line clone 6F11 deposited on Nov. 23, 2016 with Korean Cell Line Research Foundation as mPrnd#6F11 under Accession Number KCLRE-BP-00386.

Also provided are monoclonal antibodies produced by these hybridoma cell lines, and compositions comprising them together with a pharmaceutically acceptable carrier or diluent.

BRIEF DESCRIPTION OF THE DRAWINGS

FIG. 15D shows immunofluorescent images of doppel (green), CD31 (red), and DAPI (blue) in B16f10 tumor sections isolated from WT, Dpl$^{+/-}$, and Dpl$^{-/-}$ mice.

FIGS. 16A-16D show the volume of thymoma (EL4) in wild type (WT), doppel heterozygous (Dpl$^{+/-}$), and doppel homozygous (Dpl$^{-/-}$) knockout C57BL/6 mice (n=3). Tumor volume was monitored for 11 days after inoculation (FIG. 16A). Photographs of tumors isolated at the end of the experiments (FIG. 16B) and mean tumor weight (FIG. 16C) also are shown. The data are represented as mean±s.e.m.; * P<0.001 versus WT and P<0.01 between Dpl$^{+/-}$ and Dpl$^{-/-}$. FIG. 16D shows immunofluorescent images of doppel (green), CD31 (red), and DAPI (blue) in EL4 tumor sections isolated from WT, Dpl$^{+/-}$, and Dpl$^{-/-}$ mice.

FIGS. 17A-17D show the volume of colon cancer (CT26) in wild type (WT) and doppel heterozygous (Dpl$^{+/-}$) knockout C57BL/6 mice (n=3). Tumor volume was monitored for 21 days after inoculation (FIG. 17A). Photographs of tumors isolated at the end of the experiments (FIG. 17B) and mean tumor weight (FIG. 17C) are shown. The data are represented as mean±s.e.m. FIG. 17D shows immunofluorescent images of doppel (green), CD31 (red), and DAPI (blue) in EL4 tumor sections isolated from WT, and Dpl$^{+/-}$ mice.

FIGS. 18A-18D show the CD31 immunofluorescent image of wound-healing vessels (FIG. 18A) and wound-healing rates (FIG. 18B) in wild type (WT), doppel heterozygous (Dpl$^{+/-}$) and homozygous (Dpl$^{-/-}$) knockout C57BL/6 mice (n=3, mean±s.e.m.). Wounds were generated in tumor-bearing mice. Matrigel®-fibrin matrix were implanted subcutaneously in the presence of VEGF into WT, Dpl$^{+/-}$, and Dpl$^{-/-}$ knockout C57BL/6 mice (n=3). FIG. 18C shows hemoglobin levels in Matrigel®-fibrin plugs one week after implantation and FIG. 18D shows H&E staining.

FIGS. 19A-19G show that anti-doppel mAb slows tumor growth and angiogenesis. FIG. 19A and FIG. 19B show changes in the volume and weight of colon cancer (CT26) of mice treated with intravenous IgG (10 mg/kg, once a week), 5C7 anti-doppel mAb (5 and 10 mg/kg once a week), and 4D6 anti-doppel mAb (5 and 10 mg/kg once a week and 10 mg/kg twice a week) (n=5). The data are in mean±s.e.m. p<0.01, * p<0.001 vs control. *** p<0.001 between 10 mg/kg once weekly and 10 mg/kg twice weekly group. FIG. 19C and FIG. 19D show changes in the volume and weight of human colon cancer (HCT116) treated with saline (control) and intravenous 4D6 anti-doppel mAb (5 and 10 mg/kg once a week and 10 mg/kg twice a week) (n=5). FIG. 19E shows immunofluorescent images of doppel (red), CD31 (green), and DAPI (blue) in tumor sections isolated from HCT116 tumor-bearing mice treated with saline and test antibodies. FIG. 19F shows immunohistochemical staining for CD31 and FIG. 19G shows the quantification of mean vessels density in tumor sections isolated from HCT116 tumor-bearing mice treated with saline and test antibodies.

FIGS. 20A-20D show the development of anti-doppel mAb: FIG. 20A shows inhibition of TEC sprouting after incubation with cell supernatants of different clones (7D9, 1B12, 1C8, 5C7, 4D6, 6F11) of doppel-blocking mAb, and doppel-blocking mAb in the presence or absence of mouse VEGF. FIG. 20B shows the total number of sprouts from each TEC spheroid (n=50, mean s.e.m.). FIG. 20C shows immunoblots of phosphorylated-VEGFR2, total VEGFR2, and actin in TECs treated with different concentrations of purified anti-doppel mAb clones (5C7 and 4D6), when stimulated with VEGF (50 ng/mL). FIG. 20D shows inhibition of TEC sprouting after incubation with different concentrations of purified 4D6 anti-doppel mAb.

FIGS. 21A-21D relate to CT26 tumor-bearing mice treated with control and test antibodies. FIG. 21A shows photographs of CT26 tumors isolated at the end of the experiments. FIG. 21B shows immunofluorescent images of doppel (red), CD31 (green), and DAPI (blue) in tumor sections isolated from CT26 tumor-bearing mice treated with control and test antibodies. FIG. 21C shows immunohistochemical staining for CD31 and FIG. 21D shows the quantification of mean vessels density in tumor sections isolated from CT26 tumor-bearing mice treated with saline and test antibodies.

FIGS. 22A-22I show that doppel retains VEGFR2 on cell surface and promotes VEGF-signaling. FIG. 22A shows immunofluorescent images of VEGFR2 (green), CD31 (red), and DAPI (blue) in B16f10 tumor sections from WT, Dpl$^{+/-}$, and Dpl$^{-/-}$ mice and from HCT116 tumor sections treated with saline and 4D6 anti-doppel mAb (10 mg/kg twice a week). FIG. 22B shows immunoblots of total VEGFR2, doppel, and actin present in whole lungs and tumors from B16f10 tumor-bearing WT, Dpl$^{+/-}$, and Dpl$^{-/-}$ mice and from HCT116 tumor-bearing mice treated with saline and 4D6 anti-doppel mAb (10 mg/kg twice a week). FIG. 22C-FIG. 22E show blots and protein and mRNA levels of VEGFR2 and doppel following treatment with scramble siRNA and doppel siRNA in TECs isolated from squamous (TEC-SCC7) and colon (TEC-CT26) cancers. FIG. 22F shows blots representing the surface and total VEGFR2 and doppel levels in unstimulated and VEGF-stimulated (5 minutes; 100 ng/mL) HUVECs and Hu.dpl.

The rate of VEGFR2 after incubation with VEGF (25 ng/mL) in non-permeabilized HUVECs and Hu.dpl is shown in FIG. 22G, which shows the amount of VEGFR2 on the cell membrane with time in the case of HUVEC and Hu.dpl, respectively. FIG. 22H shows immunoblots of phosphorylated-VEGFR2, total VEGFR2, total doppel, and GAPDH in HUVECs and Hu.dpl, when treated with different concentrations of VEGF. FIG. 22I illustrates a proposed mechanism of action, wherein healthy endothelial cells express VEGFR2, but not doppel; tumor endothelial cells express VEGFR2 along with doppel, which acts as a supporting pillar for VEGFR2, and in the proposed mechanism of action doppel monoclonal antibody (doppel mAb) will target doppel, degrade doppel-VEGFR2 complex, inhibit VEGF signaling, and arrest tumor angiogenesis.

FIGS. 27A-27G show that recombinant doppel promotes angiogenesis. FIG. 27A shows induction of sprouting from HUVEC spheroid after incubation with different concentration of recombinant doppel (rDPl) in the presence or absence of VEGF and FIG. 27B shows the total number of sprouts from each HUVEC spheroid (n=50, mean±s.e.m.). Doppel transfected HUVEC (Hu.dpl) spheroids were used to compare in the presence of VEGF. HUVEC and Hu.dpl spheroids, dispersed in a Matrigel-fibrin matrix, were implanted subcutaneously into female SCID mice with 10 µg of rDPl in the presence or absence of VEGF. One week after transplantation, the vessels are stained.

FIG. 27C shows the 3D structure of the vascular network formed by HUVEC and Hu.dpl spheroids, stained with anti-human CD34 (red) and imaged by confocal microscopy, and FIG. 27D shows hemoglobin levels in HUVEC and Hu.dpl spheroid plugs. FIG. 27E-FIG. 27G shows the changes in the volume and weight of thymoma cancer (EL4) treated with intravenous rDPl (1 mg/kg, once per two days after day 4 of cancer cell inoculation) or inoculated with 1 and 10 µg of rDPl in doppel hetero ($Dpl^{+/-}$) knockout C57BL/6 mice (n=5). Tumor volume was monitored for 10 days after inoculation (FIG. 27E). Images of explanted tumors were taken (FIG. 27F) and tumor weight was measured (FIG. 27G). The data are in mean±s.e.m.

FIGS. 28A-28E show the expression of doppel in human dermal microvascular endothelial cells (HDMEC) one day after transfection with doppel cDNA (FIG. 28A). FIG. 28B shows immunoblots of phosphorylated-VEGFR2, total VEGFR2, total doppel, and GAPDH in transiently doppel-transfected HDMEC, when treated with VEGF. FIG. 28C shows cell proliferation and FIG. 28D and FIG. 28E show sprouting of transiently doppel-transfected HDMEC.

FIG. 29A shows blots from the immunoprecipitates (IP) of VEGFR2 and doppel in recombinant doppel (rDpl) and doppel cDNA (Dpl cDNA) transfected cells. FIG. 29B shows immunoblots of phosphorylated-VEGFR2, total VEGFR2, total doppel, and GAPDH in HUVECs, when treated with different concentrations of VEGF in the presence or absence of rDpl (1 µg/ml).

FIG. 30 shows colocalization between injected rDpl-Alexa 488 and blood vessels (FIG. 30A) and between injected rDpl-Alexa 488 and VEGFR2 (FIG. 30B) in tumor sections.

DETAILED DESCRIPTION

Figure 1:
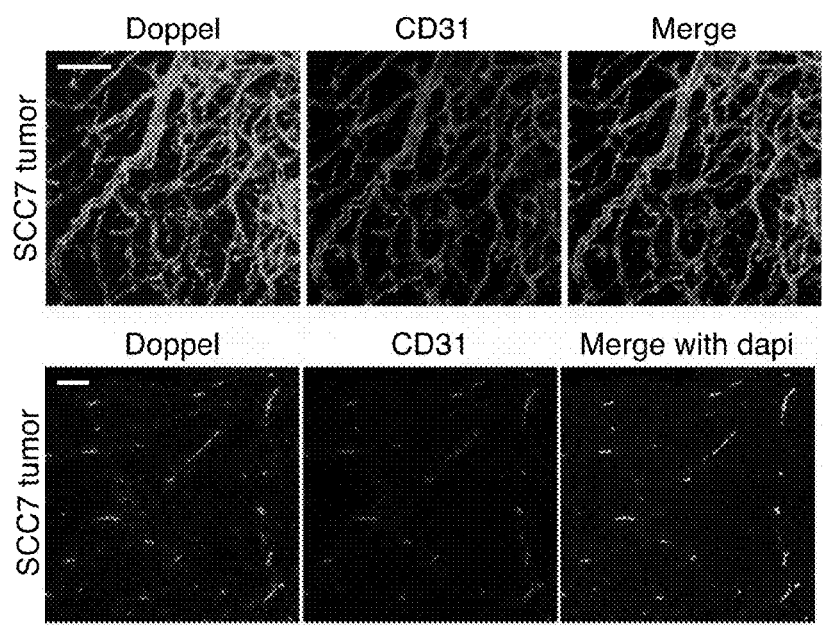
FIG. 1 represents the expression of doppel in the blood vessels of mouse xenograft tumor tissue both by whole mount (upper) and immunofluorescence (lower) staining.

The uses, compositions, and methods described herein stem from the discovery that doppel, a prion-like protein, is specific to tumoral endothelial cells (TEC), i.e., is a tumor endothelial cell (TEC) surface marker. The inventors have found that a higher expression of doppel on TEC is correlated with higher blood vessel formation. While not wanting to be bound by theory, it is believed that doppel plays a role in angiogenesis by interacting with a tyrosine kinase receptor such as VEGFR2. In this regard, the inventors have determined that doppel co-localizes and forms complexes with tyrosine kinase receptors, and that inhibition of doppel depletes membrane tyrosine kinase receptors.

Thus, in accordance with some embodiments, are doppel-targeting molecules for use in inhibiting pathological angiogenesis in a subject in need thereof, and methods based on the discovery that inhibiting the activity of doppel, such as by binding doppel, can selectively inhibit pathological doppel-tyrosine kinase receptor signaling, providing selective inhibition of pathological angiogenesis, including tumor angiogenesis and pathological angiogenesis associated with asthma, tuberculosis, atherosclerosis, pulmonary arterial hypertension (PAH), and neoplasms and neoplasm-related conditions.

Thus, in accordance with some embodiments, there are provided doppel-targeting molecules for use in inhibiting pathological angiogenesis in a subject in need thereof, such as for use in methods for inhibiting pathological angiogenesis that comprise administering a molecule that inhibits doppel activity, such as a molecule that interferes with doppel expression (e.g., doppel antisense nucleic acids) or that interferes with the interaction of doppel and a tyrosine kinase receptor (e.g., that binds to doppel, or blocks a binding site in the doppel-tyrosine kinase receptor signaling pathway).

In accordance with some embodiments, there are provided methods for inhibiting pathological angiogenesis by administering a doppel-targeting molecule that that binds to doppel, thereby inhibiting doppel-tyrosine kinase receptor signaling, and inhibiting angiogenesis. Also described are doppel-targeting molecules (e.g., molecules that bind to doppel) and pharmaceutical compositions comprising them.

Endothelial cells (EC) which line blood vessels represent an advantageous target for cancer therapy, since they may be more accessible to circulating pharmaceutical agents. Thus, targeting a tumor endothelial cell surface marker such as doppel offers a more predictable and more effective approach to cancer therapy than targeting cancer cells.

Angiogenesis-based tumor therapy has several theoretical advantages over traditional cancer therapies (such as radiation and chemotherapy). For example, (1) ECs are genetically more stable than cancer cells and do not exhibit genetic mutation, (2) the phenotypic expression of tumoral endothelium is different from that of normal endothelial cells, (3) there is a low tendency for ECs to develop resistance against chemotherapy because they are not parts of the cancer clone, and (4) the position of endothelium at the interface between blood and tumor cells makes targeting the highly expressed or up-regulated surface receptors or proteins attractive.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents, and the like to which reference is made in the following description and examples are obtainable from commercial sources, unless otherwise noted.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language ("e.g." or "such as") herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein "subject" denotes any animal in need of anti-tumor or cancer or anti-vascularization therapy, including any mammal, including human, feline, murine, canine, equine, simian, or other species. In some embodiments, the subject is a human. For example, a subject may be suffering from or at risk of developing a tumor or cancer.

As used herein, the phrases "effective amount" mean that amount that provides the specific effect for which the molecule, agent, or composition is administered. It is emphasized that an effective amount will not always be effective in treating the target condition in a given subject, even though such amount is deemed to be an effective amount by those of skill in the art. Those skilled in the art can determine and adjust such amounts in accordance with standard practices as needed to treat a specific subject and/or condition.

As used herein, the term "angiogenesis" refers to the generation of new blood vessels. As used herein, the term "tumorigenesis" refers to the growth of a tumor. As used herein, the term "pathological angiogenesis" refers to angiogenesis associated with a cancer, tumor, or other disease or condition, such as a disease or condition associated with increased vasculature, and is distinct from physiological angiogenesis, such as occurs during growth, wound healing, and the formation of granulation tissue.

As used herein, the term "angiogenic factor" includes molecules that promote angiogenesis, such as VEGFs, FGFs, PDGFB, EGF, LPA, HGF, PD-ECF, IL-8, angiogenm, TNF-alpha, TGF-beta, TGF-alpha, proliferin, and PLGF.

As used herein, the term "tyrosine kinase receptor" refers to a class of cell surface receptors with an extracellular domain that binds a ligand and an intracellular domain that phosphorylates tyrosine amino acids. Most tyrosine kinase receptors have high-affinity for a particular growth factor, cytokine, or hormone. Tyrosine kinase receptors can be classified into families based on structural similarities, e.g. the EGF receptor family, the insulin receptor family, the PDGF receptor (PDGFR) family, the FGF receptor (FGFR) family, the VEGF receptor (VEGFR) family, the HGF receptor family, the Trk receptor family, the Eph receptor family, the LTK receptor family, the TIE receptor family, the ROR receptor family, the DDR receptor family, the RET receptor family, the KLG receptor family, the RYK receptor family, and the MuSK receptor family. Non-limiting examples of tyrosine kinase receptors relevant to the methods described herein include VEGFR2, VEGFR1, VEGFR3, bFGFR, and PDGFR.

The term "VEGF receptor" or "VEGFR" as used herein refers to a cellular receptor for VEGF, ordinarily a cell-surface receptor found on vascular endothelial cells, as well as variants thereof which retain the ability to bind VEGF. One example of a VEGF receptor is the fms-like tyrosine kinase (flt) (also known as VEGFR1), a transmembrane receptor in the tyrosine kinase family. The flt receptor comprises an extracellular domain, a transmembrane domain, and an intracellular domain with tyrosine kinase activity. The extracellular domain is involved in the binding of VEGF, whereas the intracellular domain is involved in the signal transduction. Another example of a VEGF receptor is the flk-1 receptor (also referred to as KDR or VEGFR2). VEGFR2 exhibits strong tyrosine kinase receptor activity and plays an important role in angiogenesis.

As used herein, the phrases "compositions for inhibiting tumor-associated angiogenesis" and "compositions for inhibiting tumor-associated tumorigenesis" include compositions comprising therapeutic agents (molecules) that inhibit tumor-associated angiogenesis or tumorigenesis by decreasing tumor vasculature.

In the following description, details and specific embodiments are set forth in order to provide a thorough understanding of the invention, for purposes of explanation and not limitation. It will be apparent to those skilled in the art that the invention may be practiced in other embodiments that depart from the details and specific embodiments. Moreover, while the invention is described with regard to specific embodiments, and specific combinations of features, it should be understood that the invention includes all possible permutations and combinations of the various options described herein, such as all possible permutations and combinations of doppel-targeting molecules, formulations, routes of administration, target subject, effective amounts, etc.

All publications and other reference materials discussed herein are incorporated herein by reference.

Specific aspects of the invention described herein are described in Al-Hilal, et. al., *J. Clin. Invest.* 126 (4): 1251-66 (April 2016), the entire contents of which are incorporated herein by reference.

Doppel

Doppel (Dpl) is a prion-like protein, encoded by a gene named PRND, which is located near the PRNP (prion protein coding gene) locus. See, e.g, Golaniska et al., *Folia Neuropathol.* 42 (Supp. A) 47-54 (2004). Doppel is evolutionarily conserved from humans to sheep and cattle to mice, indicating an essential function. Behrens et al., *EMBO Reports* 2:347 (2001); Behrens et al, *EMBO J.* 21:3652 (2002), Human doppel is a 179 amino acid residue protein with a molecular weight of about 14 KDa (non-glycosylated). A glycosylated form of doppel with a band size of ~42 KDa has been reported in the literature. See, e.g., Al-Hilal et al., *J. Clinic. Invest.* 126:1251-1266 (2016); Peoc'h et al., *J Biol Chem.* 277(45):43071-43078 (2002)). Doppel also has been reported to exist in a dimeric form (~28 KDa).

As used herein, "doppel" refers to any doppel protein. In some embodiments, the doppel protein is glycosylated. In some embodiments, the doppel protein is not glycosylated. In some embodiments, the doppel protein is in monomeric form. In some embodiments, the doppel protein is a dimeric form.

As noted above, the uses, compositions and methods described herein stem from the inventors' discovery that doppel is a tumor endothelial cell (TEC) surface marker that plays a role in pathological angiogenesis, and that inhibiting doppel angiogenetic activity, such as by inhibiting the interaction of doppel with a tyrosine kinase receptor (e.g. VEGFR2), such as by binding doppel or otherwise, can selectively inhibit pathological angiogenesis, including tumor angiogenesis and pathological angiogenesis associated with other conditions such as asthma, tuberculosis, atherosclerosis, pulmonary arterial hypertension (PAH), neoplasms, and neoplasm-related conditions.

For example, doppel expression on TEC may be increased during pathological angiogenesis relative to its expression during normal or physiological angiogenesis conditions, or doppel expression on TEC may be associated with pathological tumor associated angiogenesis or tumorigenesis.

Doppel-Targeting Molecules

Thus, in accordance with some embodiments, there are provided molecules and methods using them for inhibiting pathological angiogenesis, wherein the molecules inhibit doppel activity, such as molecules that interfere with doppel expression or that interfere with the interaction of doppel and a tyrosine kinase receptor (e.g., inhibits doppel-VEGFR2 signaling). Such molecules are referred to herein as "doppel-targeting" molecules.

In some embodiments, the doppel-targeting molecule is a molecule that binds to doppel, thereby interfering with the interaction of doppel and a tyrosine kinase receptor, such as one or more of VEGFR2, VEGFR1, VEGFR3, bFGFR, and PDGFR. In some embodiments, the molecule binds to doppel, including molecules that preferentially bind to doppel, and/or inhibit the interaction of doppel with a tyrosine kinase receptor, such as one or more of VEGFR2, VEGFR1, VEGFR3, bFGFR, and PDGFR.

In some embodiments, the doppel-targeting molecule is an anti-doppel antibody, or a doppel-binding fragment thereof, as described below.

In some embodiments, the doppel-targeting molecule is a heparin conjugate as described in more detail below.

In some embodiments, the doppel-targeting molecule targets the doppel-VEGFR2 axis and induces its internalization and degradation.

In some embodiments, the doppel-targeting molecule binds doppel expressed on the surface of TECs. In some embodiments, the doppel-targeting molecule targets tumoral endothelial cells that express doppel.

In some embodiments, the doppel-targeting molecule evokes a therapeutic response in the tumoral endothelial cells.

In some embodiments, the doppel-targeting molecule is useful for detecting tumoral endothelial cells, such as when the doppel-targeting molecule includes or is conjugated to a detectable label.

Heparin-Containing Conjugates

In some embodiments, the doppel-targeting molecule is a heparin-containing conjugate. The term "heparin-containing conjugate" as used herein refers to conjugates comprising heparin coupled to another moiety, such as another functional moiety, directly or through a linker.

The term "heparin" as used herein refers to any species of heparin, including, but not limited to, unfractionated heparin, low molecular weight heparin, very low molecular weight heparin (vLMWH), and heparin sulfates.

In some embodiments, the functional moiety of a heparin-containing conjugate is a monomer, dimer, or oligomer of bile acids or sterols, which may be conjugated to heparin to provide increased or decreased doppel-targeting efficacy, or to target delivery to a specific site of action, such as the intestines or iluem.

Examples of suitable bile acids include, but are not limited to, cholic acid, deoxycholic acid, chenodeoxycholic acid, lithocholic acid, ursocholic acid, isoursodeoxycholic acid, lagodeoxycholic acid, glycocholic acid, taurocholic acid, glycodeoxycholic acid, glycochenodeoxycholic acid, dehydrocholic acid, hyocholic acid, hyodeoxycholic acid, and the mixtures of any two or more thereof.

Examples of suitable sterols include, but are not limited to cholestanol, coprostanol, cholesterol, epicholesterol, ergosterol, ergocalciferol, and the mixtures of any two or more thereof.

Figure 4:
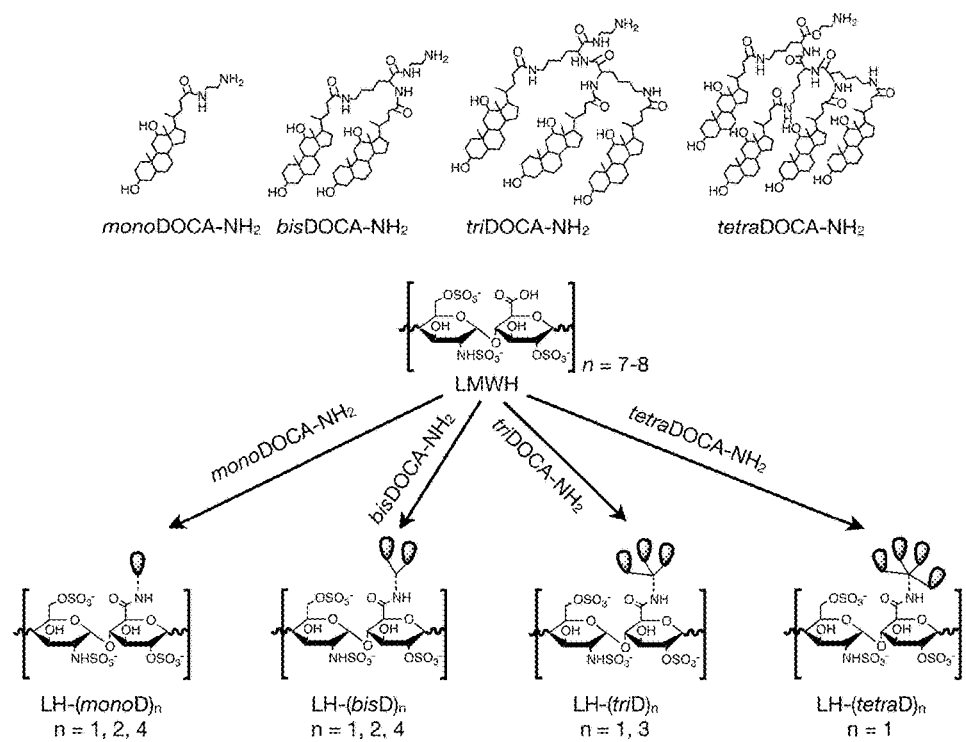
FIG. 4 shows the schematic structures of LMWH-based conjugates that are synthesized to enhance the binding affinity to doppel. Structures showing different oligomer of deoxycholic acid (oligoDOCA) derivatives, designated as monoDOCA, bisDOCA, triDOCA, and tetraDOCA. The structure of LMWH-oligoDOCA conjugates that are conjugated with the —COOH groups of saccharide units. Conjugation ratio varies from 1 to 4 molecules per molecule of LMWH.
Figure 5:
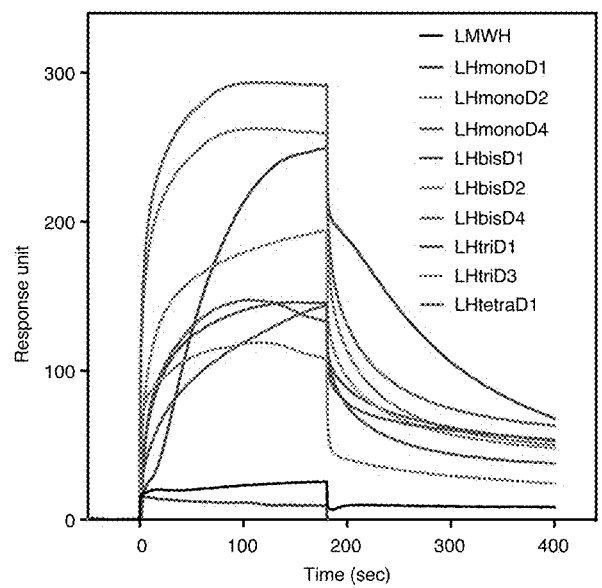
FIG. 5 shows the in vitro doppel binding of LMWH-oligoDOCA conjugates using SPR. LHbisD4, where four molecules of dimeric deoxycholic acid are conjugated to one molecule of LMWH, shows the highest response unit after binding with doppel among all the conjugates screened.
Figure 6:
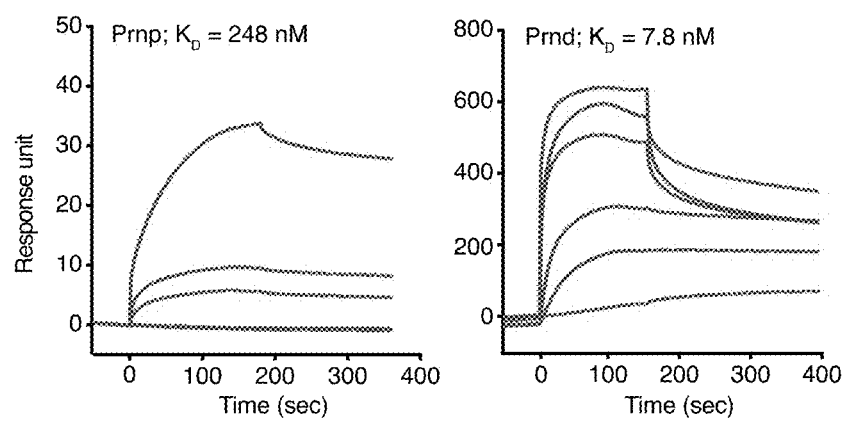
FIG. 6 shows the SPR analysis between Prnp-LHbisD4 and Prnd-LHbisD4. Dissociation rate constants are calculated from the response curves.
Figure 7:
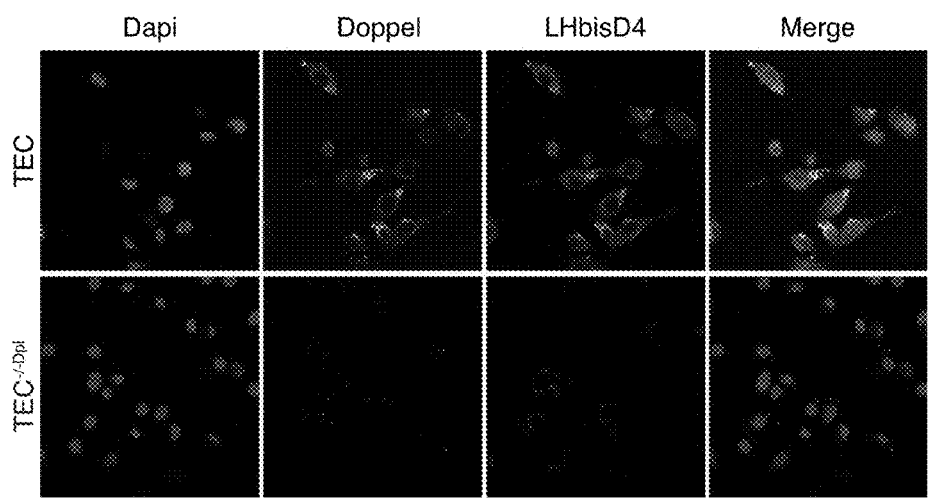
FIG. 7 shows the LHbisD4 binding to TEC and TEC$^{-/-dpl}$.
Figure 8:
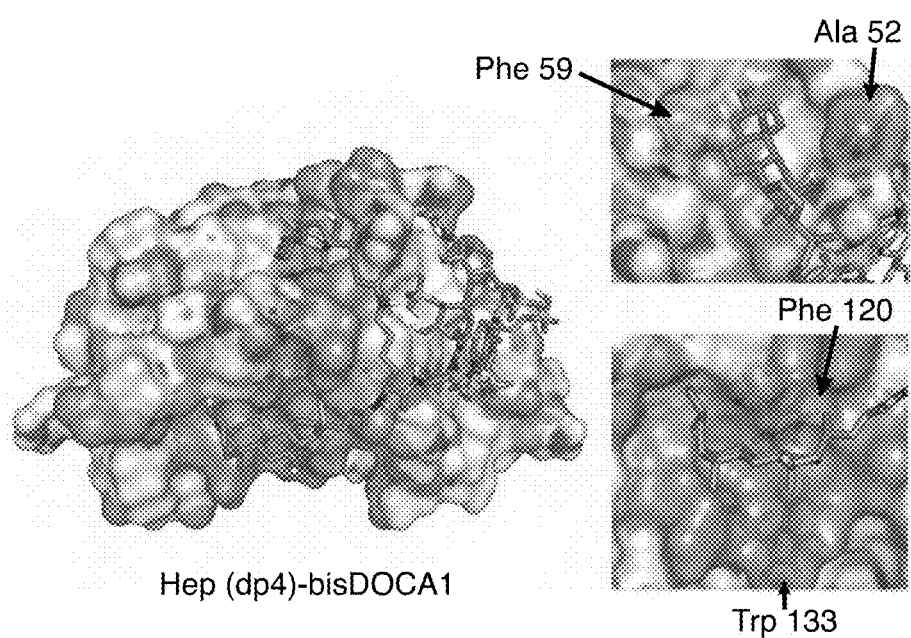
FIG. 8 shows the molecular dynamic simulation between the globular domain of doppel and LHbisD4 fragment. Fragment-based structural studies using computer simulation showed that the globular domain of doppel played a critical role in the binding of LHbisD4, since the globular domain of doppel contains hydrophobic grooves for accommodating large hydrophobic side chains of LHbisD4.
Figure 9:
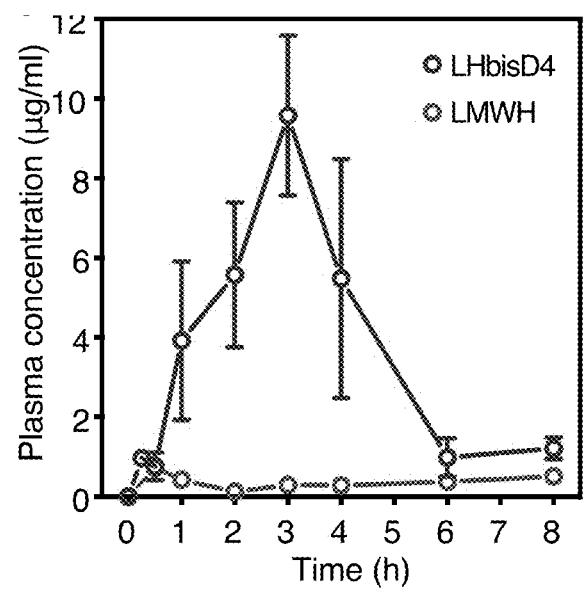
FIG. 9 shows the plasma concentration of LMWH and LHbisD4 after oral delivery to rats. Results are mean±s.e.m. LHbisD4 is orally absorbed.

An exemplary heparin conjugate useful as a doppel-targeting molecule is very low molecular weight heparin (LMWH) conjugated to one or more deoxycholic acid (DOCA) units, which form an oligomer of deoxycholic acid (oligoDOCA). Such conjugates are referred to as a LMWH-oligoDOCA conjugates. Different oligoDOCA conjugates include monoDOCA, bisDOCA, triDOCA, and tetraDOCA. LMWH-oligoDOCA conjugates may be conjugated with the —COOH groups of saccharide units. In exemplary embodiments, conjugation ratio may vary from 1 to 4 molecules per molecule of LMWH. In specific embodiments, the conjugate is LHbisD4, which is a LMWH-oligoDOCA conjugate comprising low molecular weight heparin conjugated to four repeating units of bisDOCA. See, e.g., FIG. 4; see also Al-Hilal et al., *J. Clinic. Invest.* 126:1251-1266 (2016).

Heparin-containing conjugates can be effective as doppel-targeting molecules when administered orally. Thus, in some embodiments, a heparin-conjugate (such as a LMWH-oligoDOCA conjugate) is formulated for oral administration, and used as a doppel-targeting molecule for inhibiting pathological angiogenesis wherein the heparin-containing conjugate is orally administered for efficacy as a doppel-targeting molecule.

Anti-Doppel Antibodies

In some embodiments, the doppel-targeting molecule is an anti-doppel antibody, or related species, such as a doppel-binding antibody fragment, including an antibody fragment or peptide that binds to doppel and thereby inhibits the interaction of doppel with a tyrosine kinase receptor, such as VEGFR2, VEGFR1, VEGFR3, bFGFR, and PDGFR. In specific embodiments, the anti-doppel antibody or related species binds to doppel and thereby inhibits the interaction of doppel with VEGFR2.

In accordance with any of these embodiments, the antibody may be any antibody or antibody-like molecule, including a polyclonal antibody or a monoclonal antibody, or a derivative of an antibody, such as a single chain antibody, a chimeric antibody, a humanized antibody (or other species-ized antibody modified for use in another target species), a veneered antibody, etc. The antibody may be conjugated to another moiety. The antibody may be glycosylated or aglycosylated, or have a modified glycosylation pattern.

Antibodies and antibody-like molecules suitable for use in the methods described herein can be prepared using methodology known in the art. Exemplary methods are illustrated in the Examples below.

For example, antibodies can be raised in a host (such as a mammalian host) using an antigen comprising the doppel protein or a fragment thereof, such as an N-terminal or globular domain thereof, and screened for their ability to bind to doppel and inhibit its interaction with a tyrosine kinase receptor (e.g. VEGFR2). For example, polyclonal antibodies against doppel may be prepared by collecting blood from a mammal immunized with doppel and examined for the increase of desired antibodies in the serum, and by separating serum from the blood by any conventional method. In some embodiments, serum containing the polyclonal antibodies as well as the fraction containing the polyclonal antibodies may be isolated.

The general structure of antibodies is known in the art and will only be briefly summarized here. An immunoglobulin monomer comprises two heavy chains and two light chains connected by disulfide bonds. Each heavy chain is paired with one of the light chains to which it is directly bound via a disulfide bond. Each heavy chain comprises a constant region (which varies depending on the isotype of the antibody) and a variable region. The variable region comprises three hypervariable regions (or complementarity determining regions) which are designated CDRH1, CDRH2 and CDRH3 and which are supported within framework regions. Each light chain comprises a constant region and a variable region, with the variable region comprising three hypervariable regions (designated CDRL1, CDRL2 and CDRL3) supported by framework regions in an analogous manner to the variable region of the heavy chain.

The hypervariable regions of each pair of heavy and light chains mutually cooperate to provide an antigen binding site that is capable of binding a target antigen. The binding specificity of a pair of heavy and light chains is defined by the sequence of their respective CDRs. Thus once a set of CDR sequences (i.e., the sequence of the three CDRs for the heavy and light chains) is determined which gives rise to a particular binding specificity, the set of CDR sequences can, in principle, be inserted into the appropriate positions within any other antibody framework regions linked with any antibody constant regions in order to provide a different antibody with the same antigen binding specificity.

The term "monoclonal antibody" as used herein refers to an antibody obtained by a single clone of B-lymphocytes or by a cell into which the light and heavy chain genes of a single antibody have been transfected. Monoclonal antibodies are highly specific, being directed against a single antigenic site. Furthermore, in contrast to conventional (polyclonal) antibody preparations, which typically include different antibody, directed against different determinants (epitopes), each monoclonal antibody is directed against a single determinant on the antigen. Monoclonal antibodies for use in the methods described herein can be produced by methods known to those of skill in the art, for instance, where immune cells are collected from the antigen-immunized mammal and checked for the increased level of desired antibodies in the serum and are subjected to cell fusion. The immune cells used for cell fusion are typically obtained from spleen. Other suitable parental cells to be fused with the above immunocyte include, for example, myeloma cells of mammalians, such as myeloma cells having an acquired property for the selection of fused cells by drugs. The above immunocyte and myeloma cells can be fused according to known methods, for example, the method of Milstein et al., *Methods Enzymol.* 73:3-46 (1981)). Resulting hybridomas obtained by the cell fusion may be selected by cultivating them in a standard selection medium, such as HAT medium (hypoxanthine, aminopterin and thymidine containing medium). The cell culture is typically continued in the HAT medium for several days to several weeks, the time being sufficient to allow all the other cells, with the exception of the desired hybridoma (non-fused cells), to die. Then, a standard limiting dilution can be performed to screen and clone a hybridoma cell producing the desired antibody.

In addition to the above methods, in which a non-human animal is immunized with an antigen for preparing hybridoma, human lymphocytes such as those infected by EB virus may be immunized with an antigen, antigen-expressing cells, or their lysates in vitro. Then, the immunized lymphocytes are fused with human-derived myeloma cells that are capable of indefinitely dividing, such as U266, to yield a hybridoma producing a desired human antibody that is able to bind to the antigen can be obtained. See, e.g. Unexamined Published Japanese Patent Application No. (JP-A) Sho 63-17688.

The obtained hybridomas can be transplanted into the abdominal cavity of a mouse and the ascites extracted. The obtained monoclonal antibodies can be purified by, for example, ammonium sulfate precipitation, a protein A or protein G column, DEAE ion exchange chromatography, or an affinity column to which the protein of the present invention is coupled.

"Humanized" forms of non-human (e.g., murine) antibodies can be obtained as chimeric antibodies, which contain minimal sequences derived from non-human immunoglobulin. In general, a humanized antibody will comprise at least one or two variable domains in which variable regions are derived from non-human immunoglobulin and framework regions (FR) correspond to a human immunoglobulin sequence. Thus, in some embodiments, the anti-doppel antibody comprises a human antibody framework region. Such antibodies can be prepared by know techniques. A humanized antibody optionally may contain at least a portion of an immunoglobulin constant region (Fc), typically that of a human immunoglobulin. See, e.g., Jones et al.,

*Nature* 321:522-525 (1986); Reichmann et al., *Nature* 332: 323-329 (1988); Presta, *Curr. Op. Struct. Biol.* 2:593-596 (1992).

As another method to obtain antibodies useful in the methods described herein, transgenic animals with human antibody genes may be immunized with the doppel protein, doppel protein-expressing cells, or their lysates. Resulting antibody-producing cells can be collected and fused with myeloma cells to obtain hybridoma, from which human antibodies against doppel can be prepared. Alternatively, an immune cell, such as an immunized lymphocyte, producing antibodies may be immortalized by an oncogene and used for preparing monoclonal antibodies.

Monoclonal antibodies against doppel can be also prepared using recombinant genetic engineering techniques. See, e.g., Borrebaeck C. A. K. and Larrick J. W., THERAPEUTIC MONOCLONAL ANTIBODIES (MacMillan Publishers Ltd. (1990). For example, a DNA encoding an antibody against doppel may be cloned from an immune cell, such as a hybridoma or an immunized lymphocyte producing the antibody, inserted into an appropriate vector, and introduced into host cells to prepare a recombinant doppel antibody.

As noted above, in accordance with any of these embodiments, the doppel-targeting molecule may be an antibody fragment that binds to doppel. As used herein, the term "antibody fragment" includes any doppel-binding fragment of an antibody or antibody-like molecule, including, but not limited to, $F_{ab}$ fragments, $F_{ab'}$ fragments, $F(_{ab'})_2$ fragments, and smaller fragments, diabodies, etc. An antibody "fragment" may be prepared from a full-length antibody, or may be synthesized as a "fragment" for example, using recombinant techniques.

An antibody fragment useful as a doppel-targeting molecule may comprise a portion of a full-length antibody, such as its antigen-binding domain or variable region domain. Examples of suitable antibody fragments include Fab, F(ab')2, Fv, or single chain Fv (scFv), in which Fv fragments from the heavy and light chains are ligated by an appropriate linker. See, e.g., Huston et al., *Proc. Natl. Acad. Sci. U.S.A.* 85:5879-5883 (1988)); diabodies; linear antibodies; single-chain antibody molecules; and multispecific antibodies formed from antibody fragments.

A doppel-binding antibody fragment may be generated by treating a doppel-binding antibody with an enzyme, such as papain or pepsin. Alternatively, a gene encoding a doppel antibody fragment may be constructed, inserted into an expression vector, and expressed in an appropriate host cell (see, e.g., Co et al., *J. Immunol.* 152:2968-2976 (1994); Better and Horwitz, *Methods Enzymol.* 178:476-496 (1989); Pluckthun and Skerra, *Methods Enzymol.* 178:497-515 (1989); Lamoyi, *Methods Enzymol.* 121:652-663 (1986); Rousseaux et al., *Methods Enzymol.* 121:663-669 (1986); Bird and Walker, *Trends Biotechnol.* 9:132-137 (1991)).

As used herein, the term "diabodies" refers to small antibody fragments with two antigen-binding sites, which fragments comprise a heavy chain variable domain (VH) connected to a light chain variable domain (VL) in the same polypeptide chain (VH-VL) by a linker. The linker is too short to allow pairing between the two domains on the same chain, so that the domains are forced to pair with complementary domains of another chain and create two antigen-binding sites. Diabodies are described more fully in, for example, EP 404 097; WO 93/11161; and Hollinger et al., *Proc. Natl. Acad. Sci. USA* 90:6444-6448 (1993).

As illustrated in the examples, antibodies and antibody fragments can be screened for doppel-binding activity using conventional techniques. For example, measurement of absorbance, enzyme-linked immunosorbent assay (ELISA), enzyme immunoassay (EIA), radioimmunoassay (RIA), western blot assay, and/or immunofluorescence may be used to measure doppel-binding activity. For example, for ELISA, a known anti-doppel antibody can be immobilized on a plate, doppel applied to the plate, and then a sample containing a test antibody, such as culture supernatant of antibody-producing cells or purified antibodies, can be applied. Then, a secondary antibody that recognizes the primary antibody and is labeled with an enzyme, such as alkaline phosphatase, is applied, and the plate is incubated. Next, after washing, an enzyme substrate, such as nitrophenyl phosphate, is added to the plate and the absorbance is measured to evaluate the antigen binding activity of the sample. C-terminal or N-terminal fragment of doppel protein may be used as an antigen. In another example, surface plasmon resonance analysis may be used to evaluate the activity of the antibody according to the present invention.

In some embodiments, the anti-doppel antibody binds one or more forms of doppel, such as one or more of the monomeric, dimeric, glycosylated and non-glycosylated forms discussed above. In some embodiments, the anti-doppel antibody binds one or more forms of human doppel, such as one or more of the monomeric, dimeric, glycosylated and non-glycosylated forms discussed above. In some embodiments, the anti-doppel antibody binds one or more forms of a non-human species of doppel, such as one or more of the monomeric, dimeric, glycosylated and non-glycosylated forms discussed above.

In some embodiments, the anti-doppel antibody preferentially binds to one are more of the forms of doppel described above, such a preferentially binding to one or more forms of doppel described above as compared to one or more of the other forms. In some embodiments, the anti-doppel antibody preferentially binds to one or more forms of human doppel. In some embodiments, the anti-doppel antibody preferentially binds to one or more forms of a non-human species of doppel.

In some embodiments, the anti-doppel antibody preferentially binds to one of the forms of doppel described above, such a preferentially binding to one of the forms of doppel described above as compared to the other forms. In some embodiments, the anti-doppel antibody preferentially binds to one form of human doppel. In some embodiments, the anti-doppel antibody preferentially binds to one form of a non-human species of doppel.

In some embodiments, the anti-doppel antibody binds to the glycosylated form of human doppel having a molecular weight of about 42 KDa (discussed above) with greater affinity than the non-glycosylated form of doppel. The anti-doppel antibody produced by the hybridoma cell line clone 4D6 is a specific embodiment of this type of antibody.

In some embodiments, the anti-doppel antibody binds to the non-glycosylated form of human doppel (~14 KDa) with greater affinity than the glycosylated form of doppel (~42 KDa). The anti-doppel antibodies produced by the hybridoma cell line clones 5C7, 7D9 and 1C8 are specific embodiments of this type of antibody.

In some embodiments, the anti-doppel antibody binds the dimeric form of human doppel protein (~28 KDa). The anti-doppel antibodies produced by the hybridoma cell line clones 6F11 and 1B12 are specific embodiments of this type of antibody.

In accordance with any of antibody embodiments, the anti-doppel antibody may bind to isolated forms of doppel, recombinant forms of human doppel, and/or doppel from doppel-transfected Huvec cell lysates, etc.

In some embodiments, the anti-doppel antibody is an antibody produced by a hybridoma cell line selected from any of clones 7D9, 1B12, 1C8, 5C7, 4D6, and 6F11, or a derivative of such an antibody, such as any one or more of the types of antibody derivatives discussed above, or a fragment of such an antibody or derivative thereof that binds doppel, such as any one or more of the types of antibody fragments discussed above.

Hybridoma cell lines 7D9, 1B12, 1C8, 5C7, 4D6 were deposited with the Korean Cell Line Research Foundation, Cancer Research Institute, Seoul National University College of Medicine, 28 Yongon-dong, Chongno-Gu, Seoul, 110-744, Korea, under the provisions of the Budapest Treaty on Nov. 23, 2016 under the accession numbers listed in the table below.

| Clone | Name Listed Under | Accession Number |
| --- | --- | --- |
| 7D9 | mPrnd# 7D9 | KCLRF-BP-00387 |
| 1B12 | mPrnd# 1B12 | KCLRF-BP-00383 |
| 1C8 | mPrnd# 1C8 | KCLRF-BP-00382 |
| 5C7 | mPrnd# 5C7 | KCLRF-BP-00385 |
| 4D6 | mPrnd# 4D6 | KCLRF-BP-00384 |
| 6F11 | mPrnd# 6F11 | KCLRF-BP-00386 |

In some embodiments, the an anti-doppel antibody has an amino acid sequence that is at least 85%, 90%, 95%, or 99% identical to an antibody produced by a hybridoma cell line selected from any of clones 7D9, 1B12, 1C8, 5C7, 4D6, and 6F11.

In some embodiments, the complementarity-determining regions (CDRs) of the anti-doppel antibody are at least 85%, 90%, 95%, 99%, or 100% identical to the CDRs of an antibody produced by a hybridoma cell line selected from any of clones 7D9, 1B12, 1C8, 5C7, 4D6, and 6F11.

In some embodiments, the heavy chain variable domain sequence of the anti-doppel antibody is at least 85%, 90%, 95%, 99%, or 100% identical to the heavy chain variable domain sequence of an antibody produced by a hybridoma cell line selected from any of clones 7D9, 1B12, 1C8, 5C7, 4D6, and 6F11.

In some embodiments, the light chain variable domain sequence of the anti-doppel antibody is at least 85%, 90%, 95%, 99%, or 100% identical to the light chain variable domain sequence of an antibody produced by a hybridoma cell line selected from any of clones 7D9, 1B12, 1C8, 5C7, 4D6, and 6F11.

In some embodiments, the heavy chain variable domain sequence and the light chain variable domain sequence of the anti-doppel antibody is at least 85%, 90%, 95%, 99%, or 100% identical to the heavy chain variable domain sequence and the light chain variable domain sequence, respectively, of an antibody produced by a hybridoma cell line selected from any of clones 7D9, 1B12, 1C8, 5C7, 4D6, and 6F11.

In some embodiments, the framework region sequences of the anti-doppel antibody are at least 85%, 90%, 95%, 99%, or 100% identical to the framework region sequences of an antibody produced by a hybridoma cell line selected from any of clones 7D9, 1B12, 1C8, 5C7, 4D6, and 6F11.

In some embodiments, the heavy chain variable region comprises a CDRH1 sequence comprising an amino acid sequence at least 85%, 90%, 95%, 99%, or 100% identical to the CDRH1 sequence of an antibody produced by a hybridoma cell line selected from any of clones 7D9, 1B12, 1C8, 5C7, 4D6, and 6F11.

In some embodiments, the heavy chain variable region comprises a CDRH2 sequence comprising an amino acid sequence at least 85%, 90%, 95%, 99%, or 100% identical to the CDRH2 sequence of an antibody produced by a hybridoma cell line selected from any of clones 7D9, 1B12, 1C8, 5C7, 4D6, and 6F11.

In some embodiments, the heavy chain variable region comprises a CDRH3 sequence comprising an amino acid sequence at least 85%, 90%, 95%, 99%, or 100% identical to the CDRH3 sequence of an antibody produced by a hybridoma cell line selected from any of clones 7D9, 1B12, 1C8, 5C7, 4D6, and 6F11.

In some embodiments, the light chain variable region comprises a CDRL1 sequence comprising an amino acid sequence at least 85%, 90%, 95%, 99%, or 100% identical to the CDRL1 sequence of an antibody produced by a hybridoma cell line selected from any of clones 7D9, 1B12, 1C8, 5C7, 4D6, and 6F11.

In some embodiments, the light chain variable region comprises a CDRL2 sequence comprising an amino acid sequence at least 85%, 90%, 95%, 99%, or 100% identical to the CDRL2 sequence of an antibody produced by a hybridoma cell line selected from any of clones 7D9, 1B12, 1C8, 5C7, 4D6, and 6F11.

In some embodiments, the light chain variable region comprises a CDRL3 sequence comprising an amino acid sequence at least 85%, 90%, 95%, 99%, or 100% identical to the CDRL3 sequence of an antibody produced by a hybridoma cell line selected from any of clones 7D9, 1B12, 1C8, 5C7, 4D6, and 6F11.

In some embodiments, the anti-doppel antibody includes one or more of the following characteristics:

(a) the light chain immunoglobulin variable domain sequence comprises one or more CDRs that are at least 85%, 90%, 95%, or 99% identical to a CDR of a light chain variable domain of an antibody produced by a hybridoma cell line selected from any of clones 7D9, 1B12, 1C8, 5C7, 4D6, and 6F11;

(b) the heavy chain immunoglobulin variable domain sequence comprises one or more CDRs that are at least 85%, 90%, 95%, or 99% identical to a CDR of a heavy chain variable domain of an antibody produced by a hybridoma cell line selected from any of clones 7D9, 1B12, 1C8, 5C7, 4D6, and 6F11;

(c) the light chain immunoglobulin variable domain sequence is at least 85%, 90%, 95%, or 99% identical to a light chain variable domain of an antibody produced by a hybridoma cell line selected from any of clones 7D9, 1B12, 1C8, 5C7, 4D6, and 6F11; and/or (d) the heavy chain immunoglobulin variable domain sequence is at least 85%, 90%, 95%, or 99% identical to a heavy chain variable domain of an antibody produced by a hybridoma cell line selected from any of clones 7D9, 1B12, 1C8, 5C7, 4D6, and 6F11.

In other embodiments, one or more amino acid residues in a CDR of the antibodies disclosed herein are substituted with another amino acid. The substitution may be "conservative" in the sense of being a substitution within the same family of amino acids, based on the following family groupings:

(1) Amino acids with basic side chains: lysine, arginine, histidine.

(2) Amino acids with acidic side chains: aspartic acid, glutamic acid (3) Amino acids with uncharged polar side chains: asparagine, glutamine, serine, threonine, tyrosine.

(4) Amino acids with nonpolar side chains: glycine, alanine, valine, leucine, isoleucine, proline, phenylalanine, methionine, tryptophan, cysteine.

In other embodiments, one or more amino acid residues are added to or deleted from one or more CDRs of an antibody. Such additions or deletions may occur at one or more of the N or C terminus of the CDR or at a position within the CDR.

By varying the amino acid sequence of the CDRs of an anti-doppel antibody by addition, deletion or substitution of amino acids, various effects such as increased binding affinity for the target antigen may be obtained.

The constant regions of anti-doppel antibodies may also be varied. For example, antibodies may be provided with Fc regions of any isotype: IgA (IgA1, IgA2), IgD, IgE, IgG (IgG1, IgG2, IgG3, IgG4) or IgM.

In some embodiments, the heavy chain constant domain sequence of the anti-doppel antibody is at least 85%, 90%, 95%, 99%, or 100% identical to the heavy chain constant domain sequence of an antibody produced by a hybridoma cell line selected from any of clones 7D9, 1B12, 1C8, 5C7, 4D6, and 6F11.

In some embodiments, the light chain constant domain sequence of the anti-doppel antibody is at least 85%, 90%, 95%, 99%, or 100% identical to the light chain variable domain sequence of an antibody produced by a hybridoma cell line selected from any of clones 7D9, 1B12, 1C8, 5C7, 4D6, and 6F11.

In some embodiments, the heavy chain constant domain sequence and the light chain constant domain sequence of the anti-doppel antibody is at least 85%, 90%, 95%, 99%, or 100% identical to the heavy chain constant domain sequence and the light chain constant domain sequence, respectively, of an antibody produced by a hybridoma cell line selected from any of clones 7D9, 1B12, 1C8, 5C7, 4D6, and 6F11.

In some embodiments, the anti-doppel antibody comprises a heavy chain variable domain sequence and a light chain variable domain sequence that together form an antigen binding site that binds to doppel. In some embodiments, the anti-doppel antibody binds to an epitope bound by an antibody produced by a hybridoma cell line selected from any of clones 7D9, 1B12, 1C8, 5C7, 4D6, and 6F11. In some embodiments, the anti-doppel antibody binds to doppel with similar specificity and sensitivity profiles as the antibodies on which they are based (e.g., an antibody produced by a hybridoma cell line selected from any of clones 7D9, 1B12, 1C8, 5C7, 4D6, and 6F11).

Compositions

Also described herein are compositions comprising one or more doppel-targeting molecules. In some embodiments, the compositions comprise a pharmaceutically acceptable excipient or carrier, such as a carrier suitable for the intended route of administration.

The composition may be prepared for any route of administration, including any oral; parenteral, or local route of administration. In some embodiments, the composition is suitable for injection or infusion, such as for intravenous injection or infusion, such as being prepared as a sterile composition for injection or infusion. In other embodiments, the composition is suitable for oral administration, such as being prepared in a liquid or solid oral dosage form (such as a solution, syrup, powder, granule, tablet, capsule, suspension, emulsion, or oral spray). In other embodiments, the pharmaceutical composition is suitable for inhalation, such as being in the form of a solution or powder suitable for nasal or peroral inhalation. In other embodiments, the pharmaceutical composition is suitable for rectal or vaginal administration, such as being in a suppository formulation. In other embodiments, the composition is suitable for topical or transdermal administration, such as being in a solution, emulsion, gel, or patch. Appropriate components and excipients for such compositions are known in the art.

Thus, in some embodiments, the doppel-targeting molecule is formulated for oral administration, subcutaneous injection, intravenous injection or infusion, intraocular injection, intradermal injection, intramuscular injection, intraperitoneal injection, intratracheal administration, inhalation, intranasal administration, sublingual administration, buccal administration, rectal administration, vaginal administration, or topical administration.

In some embodiments, the doppel-targeting molecule is formulated for oral administration. As noted above, the LMHW-oligoDOCA conjugates may be particularly suitable for oral administration. In some embodiments, the doppel-targeting molecule is formulated for oral administration and selective absorption in the intestines or ileum. For example, the LMHW-oligoDOCA conjugates doppel-targeting molecule may localize in the intestines or ileum. Additionally or alternative, the formulation may provide targeted release of the doppel-targeting molecule in the intestines or ileum, such as by using pH-controlled and/or delayed release formulation techniques that are known in the art.

In some embodiments, the doppel-targeting molecule is formulated for intravenous injection. Antibodies and antibody fragments typically are administered by intravenous injection to avoid degradation in the digestive tract, but could be formulated for oral delivery by, for example, formulating the antibodies/fragments in a manner that protects them from digestive enzymes, such as by using formulation techniques that are known in the art.

Examples of formulations for parenteral administration include sterilized aqueous solutions, water-insoluble solutions, suspensions, emulsions, lyophilized formulations, and suppositories. Non-aqueous solutions and suspensions may include, for example, propylene glycol, polyethylene glycol, a plant oil such as olive oil, or injectable ester such as ethyloleate. A base for a suppository formulation may include, for example, witepsol, macrogol, Tween 61, cacao butter, laurin butter, glycerogelatin or the like.

Formulations for oral delivery may comprise a poloxamer, labrasol, polyethylene glycol, and mixtures thereof.

In some embodiments, the composition comprises an effective amount of a doppel-targeting molecule to interfere with the interaction of doppel and a tyrosine kinase receptor, such as VEGFR2, VEGFR1, VEGFR3, bFGFR, and PDGFR. In some embodiments, the composition comprises an effective amount of a doppel-targeting molecule to decrease pathological angiogenesis. In some embodiments, the composition comprises an effective amount of a doppel-targeting molecule to decrease tumor angiogenesis. In some embodiments, the composition comprises an effective amount of a doppel-targeting molecule to decrease pathological vasculature. In some embodiments, the composition comprises an effective amount of a doppel-targeting molecule to decrease tumor vasculature. In some embodiments, the composition comprises an effective amount of a doppel-targeting molecule to decrease tumor angiogenesis.

In some embodiments, the composition comprises an effective amount of a doppel-targeting molecule to decrease angiogenesis associated with asthma. In some embodiments, the composition comprises an effective amount of a doppel-targeting molecule to decrease angiogenesis associated with tuberculosis. In some embodiments, the composition comprises an effective amount of a doppel-targeting molecule to decrease angiogenesis associated with atherosclerosis. In some embodiments, the composition comprises an effective amount of a doppel-targeting molecule to decrease angiogenesis associated with pulmonary arterial hypertension (PAH). In some embodiments, the composition comprises an effective amount of a doppel-targeting molecule to decrease angiogenesis associated with a neoplasm or neoplasm-related condition.

In some embodiments, the compositions are effective to evoke a therapeutic response in tumoral endothelial cells.

In some embodiments, the compositions are effective to detect tumoral endothelial cells, such as when the doppel-targeting molecule includes or is conjugated to a detectable label.

In some embodiments, the compositions are effective to evoke a therapeutic response to a neoplasm or a neoplasm-related condition, such as breast carcinomas, lung carcinomas, gastric carcinomas, esophageal carcinomas, colorectal carcinomas, liver carcinomas, ovarian carcinomas, arrhenoblastomas, cervical carcinomas, endometrial carcinomas, endometrial hyperplasias, endometriosis, fibrosarcomas, choriocarcinomas, head and neck cancers, nasopharyngeal carcinomas, laryngeal carcinomas, hepatoblastomas, Kaposi's sarcomas, melanomas, skin carcinomas, hemangiomas, cavernous hemangiomas, hemangioblastomas, pancreas carcinomas, retinoblastomas, astrocytomas, glioblastomas, Schwannomas, oligodendrogliomas, medulloblastomas, neuroblastomas, rhabdomyosarcomas, osteogenic sarcomas, leiomyosarcomas, urinary tract carcinomas, thyroid carcinomas, Wilm's tumor, renal cell carcinomas, prostate carcinomas, abnormal vascular proliferation associated with phakomatoses, edemas (such as that associated with brain tumors), and/or Meigs' syndrome In some embodiments, the compositions disclosed herein are used for inhibiting angiogenesis in a subject in need thereof. In some embodiments, the subject is suffering from or at risk of developing a disease or condition involving doppel-tyrosine kinase receptor signaling (such as doppel-VEGFR2 signaling), such as a tumor or cancer or a disease or condition associated with increased vascularization, such as asthma, tuberculosis, atherosclerosis, pulmonary arterial hypertension (PAH), or a neoplasm or neoplasm-related condition.

Methods of Identifying Doppel-Targeting Molecules

Exemplary doppel-targeting molecules are described above. Additional doppel-targeting molecules can be identified by screening methods, such as those described below and illustrated in the examples below.

Suitable methods may include assessing the binding of a test molecule to a doppel protein (or a fragment thereof that forms a complex with a trysoine kinase inhibitor e.g. VEGFR2)) as illustrated in the examples below. Such methods may additionally or alternatively include culturing endothelial cells where doppel and the tyrosine kinase inhibitor constitutively interact with each other in the presence or absence of a test agent that binds the doppel protein or fragment thereof and detecting one or more of the internalization of the tyrosine kinase inhibitor and/or the degradation of the tyrosine kinase inhibitor, and selecting a test molecule that inhibits the internalization of the tyrosine kinase inhibitor and/or promotes the degradation of the tyrosine kinase inhibitor, as compared with the internalization and/or degradation detected in the absence of the test molecule. Additionally or alternatively, doppel-blocking activity can be detected, for example, by assaying the inhibition of phosphorylation and degradation of the tyrosine kinase inhibitor. Additionally or alternatively, doppel-blocking activity can be detected, for example, by assaying the suppression of endothelial cell sprouting, which can be detected, for example, by assaying the sprout number formed in endothelial cell spheroids and comparing the number of sprouts arising in a control group. Various methods and embodiments are illustrated in the examples below.

Any doppel protein can be used to assess binding of the test molecule. In specific embodiments, the doppel protein or fragment thereof forms a complex with the target tyrosine kinase inhibitor, such as VEGFR2 protein.

Any medium may be used for culturing endothelial cells where doppel and the tyrosine kinase inhibitor constitutively interact with each other in the presence or absence of a test agent. For example, cell extracts, cell culture supernatants, products of fermenting microorganism, extracts of marine organisms, plant extracts, etc., can be used.

Inhibiting Pathological Angiogenesis

As discussed above, the doppel-targeting molecules and compositions described herein are useful for inhibiting pathological angiogenesis and treating related diseases or conditions, in a subject in need thereof. Thus, such uses and methods are provided herein.

As noted above, the term "subject" as used herein refers to any mammal, including human, feline, murine, canine, equine, simian, or other species. In some embodiments, the subject is a human.

As used herein, "treating" includes reducing, slowing, or retarding pathological angiogenesis (or tumorigenesis), even if some pathological angiogenesis (or tumorigenesis) still occurs, and/or reducing, slowing, or retarding increased vasculature even if some pathological increased vasculature still occurs.

The doppel-targeting molecules and compositions described herein are useful in inhibiting pathological angiogenesis in subjects with a disease or condition involving doppel or doppel-tyrosine kinase receptor signaling, or a disease or condition indicated by increased vascularization. Non-limiting examples of such diseases or conditions include tumors, cancers, such as, but not limited to, angiogenic cancers; atherosclerosis; tuberculosis; asthma, and pulmonary arterial hypertension (PAH). Thus, the disclosed methods and doppel-targeting molecules and/or compositions may be useful for treating various neoplastic and non-neoplastic diseases and disorders.

The doppel-targeting molecules and compositions disclosed herein are also useful in generating a therapeutic response against tumoral endothelial cells (TECs) and, thus, in the treatment of diseases or conditions characterized by the presence of these cells.

The doppel-targeting molecule and compositions described herein are useful in treating neoplasms and neoplasm-related conditions.

The term "neoplasm" as used herein refers to an abnormal growth of tissue; which upon formation of a mass is known as a tumor. Neoplasms may be benign or malignant. Malignant neoplasms are generally referred to as cancer.

Neoplasms and neoplasm-related conditions that are amenable to treatment include breast carcinomas, lung carcinomas, gastric carcinomas, esophageal carcinomas, colorectal carcinomas, liver carcinomas, ovarian carcinomas, arrhenoblastomas, cervical carcinomas, endometrial carcinomas, endometrial hyperplasias, endometriosis, fibrosarcomas, choriocarcinomas, head and neck cancers, nasopharyngeal carcinomas, laryngeal carcinomas, hepatoblastomas, Kaposi's sarcomas, melanomas, skin carcinomas, hemangiomas, cavernous hemangiomas, hemangioblastomas, pancreas carcinomas, retinoblastomas, astrocytomas, glioblastomas, Schwannomas, oligodendrogliomas, medulloblastomas, neuroblastomas, rhabdomyosarcomas, osteogenic sarcomas, leiomyosarcomas, urinary tract carcinomas, thyroid carcinomas, Wilm's tumor, renal cell carcinomas, prostate carcinomas, abnormal vascular proliferation associated with phakomatoses, edemas (such as that associated with brain tumors), and Meigs' syndrome.

Thus, provided herein doppel-targeting molecules and compositions comprising them for use in methods of inhibiting pathological angiogenesis in a subject in need thereof, such as a subject suffering from or at risk of developing any one or more of the conditions mentioned above, as well as such methods. The uses and methods comprise administering an effective amount of a doppel-targeting molecule or compositions as described herein to a subject in need thereof. In some embodiments, the effective amount is effective to interfere with the interaction of doppel and a tyrosine kinase receptor, such as VEGFR2, VEGFR1, VEGFR3, bFGFR, or PDGFR. In specific embodiments, the effective amount is effective to interfere with the interaction of doppel and VEGFR2. In some embodiments, the effective amount is effective to decrease the vasculature of a tumor. In some embodiments, the effective amount is effective to evoke a therapeutic response in tumoral endothelial cells. In some embodiments, the effective amount is effective to reducing, slowing, or retarding pathological angiogenesis or tumorigensis. In some embodiments, the effective amount is effective to decrease angiogenesis associated with asthma. In some embodiments, the effective amount is effective to decrease angiogenesis associated with tuberculosis. In some embodiments, the effective amount is effective to decrease angiogenesis associated with atherosclerosis. In some embodiments, the effective amount is effective to decrease angiogenesis associated with pulmonary arterial hypertension (PAH). In some embodiments, the effective amount is effective to decrease angiogenesis associated with a neoplasm or neoplasm-related disorder.

The doppel-targeting molecules may be administered via any route of administration, including any parenteral or local route of administration. In some embodiments, the method comprises administering the doppel-targeting molecule by oral administration, subcutaneous injection, intravenous injection or infusion, intraocular injection, intradermal injection, intramuscular injection, intraperitoneal injection, intratracheal administration, inhalation, intranasal administration, sublingual administration, buccal administration, rectal administration, vaginal administration, or topical administration.

In some embodiments, the method comprises administering the doppel-targeting molecule by oral administration. In some embodiments, the method comprises administering the doppel-targeting molecule by intravenous injection.

In some embodiments, the methods include treating the subject with an additional therapy. For example, treatment methods may include administering a chemotherapeutic agent to the subject, or providing radiation therapy. As used herein, the term "chemotherapeutic agent" refers to a molecule useful to treat cancer, such as a small molecule chemical compound used to treat cancer. Non-limiting examples of chemotherapeutic agents include but are not limited to alkylating agents, anti-metabolites, anti-tumor antibiotics, plant alkaloids/microtubule inhibitors, DNA linking agents, biologics, bisphosphonates, hormones, and other drugs known to be useful to treat cancer. Non-limiting examples of chemotherapeutic agents include aminoglutethimide, amsacrine, anastrozole, asparaginase, beg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

Methods of Detecting Doppel

The doppel-targeting molecules and compositions described herein also are useful as agents for detecting the presence of doppel, such as for determining whether doppel is associated with a particular disease or condition, or is being expressed in a subject, or is being expressed by TEC of a subject.

For such uses, a doppel-targeting molecule is administered to a subject and/or to a biological sample taken from the subject, and then any binding between the doppel-targeting molecule and any doppel present in the subject or sample is detected. In some embodiments, the doppel-targeting molecule includes or is conjugated to a detectable label. In other embodiments, binding between the doppel-targeting molecule and any doppel present in the subject or sample is detected using an antibody specific for the doppel-targeting molecule and/or the doppel-targeting molecule/doppel complex.

If doppel is determined to be associated with the disease or condition, or is determined to be expressed by TEC of a subject, the subject could be treated by the methods described herein.

In specific embodiments, the subject may be any described above, such as being at risk of developing a tumor, at risk of developing a disease or condition selected from cancer, atherosclerosis, tuberculosis, asthma, and pulmonary arterial hypertension (PAH), and/or at risk of developing a neoplasm or neoplasm-related condition, as described above.

EXAMPLES

The following examples illustrate specific embodiments, and are illustrative only.

Example 1: Sorting of Tumoral Endothelial Cells (TEC) for Evaluating Doppel Expression This example describes methods of purifying endothelial cells from different tumor tissue types.

Tumoral endothelial cells were isolated using a double marker following a published procedure with some modifications. Briefly, tumors were grown subcutaneously in the flank of $C_3H/HeN$ mice and resected, minced using two surgical blades, and digested in 9 mL collagenase and 1 mL dispase solution per gram of tissue. Tissues were incubated for 30 minutes in a 37° C. water bath, under continuous agitation. Subsequently, 75 uL DNaseI solution per 10 ml cell suspension was added and incubated for another 30 minutes at 37° C. with continuous agitation. Digested tissues were sieved through a 100-μm cell strainer and single cells were separated. Cells were collected by centrifugation at 400×g for 7 min at room temperature. To remove red blood cells, granulocytes, nonvital cells and cell debris, the cells were resuspended in 10 mL Ficoll separation medium (per gram of starting material) and carefully layered in the suspension on 7.5 mL Ficoll-Paque (pre-warmed to room temperature). The interphase-containing viable cells were transferred into a fresh tube. Cells were collected into FACS tubes, and incubated with anti-mouse CD31-PE and anti-mouse CD34-FITC antibodies (at a final concentration of 2 µg/mL). FACS machine was prepared by adjusting conditions with a sheath fluid pressure of 29.9 psi, a sorting frequency of 44 kHz, and a plate voltage of 3,500 V. Collected cells were suspended in 10 ml ECGM containing 10% FBS and centrifuged. Then cells were plated in 0.2% gelatin-coated 100 mm dishes and cultured overnight in normal ECGM supplemented. The next day, the media was replaced with supplemented ECGM containing 10% FBS. Cells were grown until confluent.

Example 2: Immunofluorescence and Whole Mount Staining for Doppel Expression

Tumors were dissected and cut into pieces (plugs) of approximately 2 mm×2 mm using a scalpel. The plugs were fixed in methanol containing 25% DMSO for 24 hours at 4° C. in a 50 ml reaction tube. The plugs were washed three times (at least 30 minutes each time) with sterile PBS at 4° C. with gentle agitation. The plugs were blocked for 3 hours with 5% BSA at 4° C. under gentle agitation. The tumor plugs were incubated in blocking buffer containing the primary antibody overnight at 4° C. under gentle agitation. On the next day, the plugs were washed three times with TBST for 3 hours at 4° C. under gentle agitation. The plugs were incubated in blocking buffer (5% BSA in TBST) containing the fluorescence-labeled secondary antibody overnight at 4° C. under gentle agitation. After washing for 3 hours at 4° C. under gentle agitation the plugs were stained with Hoechst dye. The plugs were embedded in mounting medium and slides were sealed with pertex to prevent drying out. The three dimensional structure of the capillary network was analyzed by confocal microscopy (Carl Zeiss LSM710, Leica DM IRB/E, Leica Co., Germany). For doppel and CD31 detection, sections were simultaneously stained with goat anti-mouse doppel followed by Alexa488-linked donkey anti-goat and PE-linked rat anti-mouse CD31.

To evaluate doppel expression at the molecular level, TECs were isolated from the highly angiogenic squamous cell carcinoma (SCC7) grown in mice. Whole-mount and immunofluorescence staining revealed that most of the vasculatures expressed doppel at high levels in primary tumors (FIG. 1).

Example 3: Quantitative PCR for Doppel Expression mRNA was purified using the Quick Prep Micro mRNA purification kit (Amersham, Piscataway, N.J.). Single-stranded cDNA was generated using the Superscript III first strand synthesis system (Invitrogen) following the manufacturer's directions. Quantitative PCR was performed with an MX4000 using Brilliant SYBR Green QPCR Master Mix, and threshold cycle numbers were obtained using MX4000 software v. 4.20 (Stratagene, La Jolla, Calif.). Conditions for amplification were: one cycle of 95° C. for 10 minutes followed by 40 cycles of 95° C. each for 20 seconds; 56° C., 30 seconds; and 72° C., 30 seconds. Quantitative PCRs were performed in triplicate, and threshold cycle numbers were averaged. Gene expression was normalized to that of the 70 Kd U1 small nuclear ribonucleoprotein polypeptide A (Snrnp70), a gene uniformly expressed in all ECs as assessed by SAGE. Relative expression was calculated using the equation $2^{(Rt-Et)}/2^{(Rn-En)}$, where Rt is the threshold cycle number observed in the experimental sample for Snrnp70, Et is the threshold cycle number observed in the experimental sample for the gene of interest (GOI), Rn is the average threshold cycle number observed for Srnp70 in B.End.3 or HUVEC samples, and En is the average threshold cycle number observed for the GOI in B.End.3 or HUVEC samples. Primers used were
mouse doppel:

```
forward:    GGACATCGACTTTGGAGCAGAG (SEQ ID NO: 1);
reverse:    CAGCATCTCCTTGGTCACGTTG (SEQ ID NO: 2),
``` human doppel:

```
forward:    GATGGCATCCACTACAACGGCT (SEQ ID NO: 3);
reverse:    GTTGTCTGGCTTCTGGAACTCC (SEQ ID NO: 4),
``` mouse Snrnp70:

```
forward:    GCCTTCAAGACTCTGTTCGTGG (SEQ ID NO: 5);
reverse:    CTCGATGAAGGCATAACCACGG (SEQ ID NO: 6),
``` human Snrnp70:

```
forward:    TCAAGACTCTCTTCGTGGCGAG (SEQ ID NO: 7),
reverse:    GGCTTTCCTGACCGCTTACTGT (SEQ ID NO: 8).
```

Figure 2:
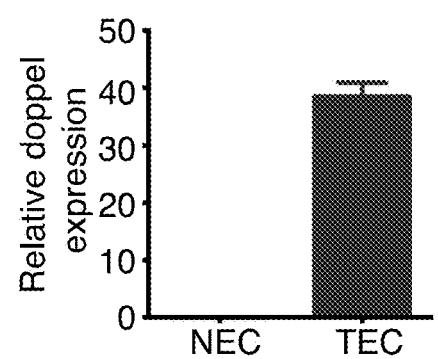
FIG. 2 represents the relative mRNA expression of doppel in the mouse normal endothelial cells (EC) and tumoral ECs (mean±s.e.m.).

Quantitative RT-PCR analysis revealed that the transcript level was approximately 38-fold higher in the purified TECs from SCC7 than in the normal mouse endothelium (FIG. 2). Taken together, these data indicated that doppel expression, at both the transcript and protein levels, ectopically increases during tumor formation and was specific to TECs within the tumors.

Example 4: Generation of TEC Spheroid and Subcutaneous Implantation in Mice

The spheroid-based in vivo angiogenesis assay was performed according to a published procedure. Briefly, 8×10$^6$ TECs or TEC$^{-/-dpl}$ were suspended in 200 mL media containing 20% methocel solution and 80% culture medium. Cells were divided into non-adherent plastic square petri dishes, 25 µL for each spheroid. Spheroids formed by TECs or TEC$^{-/-dpl}$ were harvested and mixed in a matrigel/fibrin mixture that contained mouse VEGF and bFGF. TECs or TEC$^{-/-dpl}$ spheroids (1000 spheroids per plug) were inoculated subcutaneously in the flank of each female SCID mouse (5-6 weeks, Jungang Animal Lab, Korea) or female Balb/c nude mice (Orinet bio, Seongnam, Korea). The spheroids were allowed to grow for 3 weeks. Cy5.5-labeled LMWH, at a dose 2.5 mg/kg, was injected intravenously, and at 2 hours after injection, its accumulation at the site of TEC implantation was checked using Optimax-MX3 (GE Medical Systems, Milwaukee, Wis.). In other experiments, Cy5.5-labeled LHbisD4, at a dose 10 mg/kg, was administered orally, and its distribution was also checked as described previously. The matrix plug was removed and part of the plugs was analyzed for microvessel density and drug accumulation by immunofluorescence staining.

Figure 3:
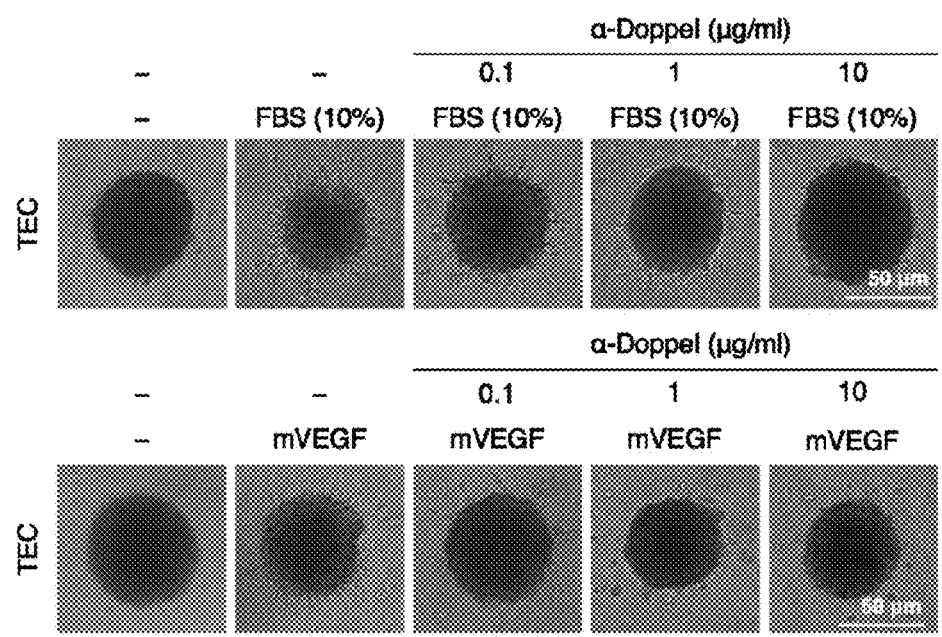
FIG. 3 shows the dose dependent inhibition of TEC sprouting by anti-doppel antibody when stimulated with either 10% fatal bovine serum, or mouse VEGF. Results are mean±s.e.m.; the scale bar represents 50 µm.

Anti-doppel dose-dependently abrogated either FBS or mVEGF-induced sprouting of TEC spheroids (FIG. 3). These data suggested that doppel regulates VEGFR2 signaling in endothelial cells.

Example 5: Synthesis of Doppel-Binding LMWH-DOCA Conjugates

This example describes the synthesis of several bile-acid (deoxycholic acid)-based heparin conjugates useful as doppel-targeting molecules as described herein.

Deoxycholic acid (DOCA) derivatives were synthesized by the chemical conjugation of deoxycholic acid and lysine, or lysine substituents, containing 2-4 amine groups using a building block method. They are referred to as the monomeric, dimeric, trimeric, and tetrameric deoxycholic acids (monoDOCA, bisDOCA, triDOCA, tetraDOCA, respectively) (FIG. 4). Prior to conjugating with LMWH, DOCA derivatives were reacted with ethylenediamine (EDA) to introduce a focal primary amine at each DOCA derivative. LMWH-DOCA conjugates were synthesized by chemical coupling of hydrophilic LMWH backbone with amine conjugated DOCA derivatives (monoDOCA-$NH_2$, bisDOCA-$NH_2$, triDOCA-$NH_2$, and tetraDOCA-$NH_2$). LMWH (100 mg) was dissolved in 3.125 mL FA at an accelerated temperature. DOCA derivatives were also dissolved in a co-solvent system of DMF/FA. The carboxylic groups of LMWH were activated using EDAC/NHS and reacted with DOCA derivatives at different feed model ratios ranging from 1:12 at 4° C. for 12 hours. The reacted materials were then precipitated in an excess of cold ethanol followed by drying in vacuum after centrifugation. The dried heparin conjugates were dissolved in water before being lyophilized. The synthesis of LMWH-DOCA conjugates was confirmed using $^1$H NMR, which showed specific amide bonds and bile acid peaks in the specific ppm range. Relative anticoagulant activity of the LMWH-DOCA conjugates was determined by a kinetic method using an anti-factor Xa (anti-FXa) chromagenic assay kit and a chromagenic substrate (S2222) sensitive to FXa. The conjugation ratio was determined as described by Fini et al with some modifications.

Example 6: Measurement of Binding Affinity Between Doppel and LMWH-DOCA Conjugates This example describes a method of assessing the dissociation rate constant between doppel and LMWH-DOCA conjugates.

Affinity measurements of LMWH and LMWH-DOCA conjugates with Prnp and Prnd (doppel) were performed by the surface plasmon resonance on a BIAcore T100 (GE Healthcare). Using the standard EDAC-NHS coupling method, recombinant proteins were immobilized at a density of 4000-7000 onto a sensor chip (GE Healthcare). Measurements were performed at a flow rate of 20 μL/min, and 50 mM NaOH was used to regenerate the chip surface after each cycle of analysis. Each concentration was analyzed in duplicate. Kinetic analysis of the data obtained was performed using BIAcore T100 evaluation software (GE Healthcare).

New heparin-based compounds (conjugates of heparin with deoxycholic acids) were designed. LHbisD4, a chemical conjugate of four dimeric DOCA molecules to one LMWH molecule, was selected for further study. LHbisD4 exhibited a higher binding affinity to doppel ($K_D$=7.8 nM) than LMWH or other bile acid-based conjugates (FIG. 5). In addition, unlike LMWH, LHbisD4 showed no anticoagulant activity, nor changes in binding affinity to cellular prion protein, Prnp, when compared to LMWH (FIG. 6). LHbisD4 binding was also remarkably reduced in $TEC^{-/-dpl}$ than TEC (FIG. 7). Fragment-based structural studies using computer simulation showed that the globular domain of doppel played a critical role in binding with LHbisD4, since this region contains hydrophobic grooves for capturing large hydrophobic side-chains of LHbisD4 (FIG. 8).

Example 7: Pharmacokinetics and Bio-Distribution Studies of the LMWH-DOCA Conjugate, LHbisD4

This example describes that the doppel-targeting molecule LHbisD4 can be administered orally for tumor-specific vascular targeting.

For pharmacokinetic experiments, Sprague Dawley (SD) rats (male, weighed 250-260 g) were randomly divided into two groups (n=4-5 for each group) for LMWH and LHbisD4. Treated samples, at a dose of 10 mg/kg, were administered orally mixing with labrasol and Poloxamar 188 (BASF Aktiengesellschaft, Germany). Blood was collected at 15 minutes, 30 minutes, and 1, 2, 3, 4, 6, and 8 hours after the drug administration. Plasma was isolated by centrifugation at 4,000×g for 20 minutes. The amount of drugs in the plasma was measured by heparin-orange chemosensor kit. Heparin orange chemosensor kit (Heparin Orange G26; MW 675.57), obtained from Professor Yang-tae Chung from Lumino Genomics Laboratory of National University of Singapore, was used to detect the plasma concentrations of the samples by previously described methods. In brief, heparin orange, a chemo sensor material that reacts with heparin conjugates, has a reaction pattern that is mostly charge-charge interactions, and the resulting complex emits luminescence.

Biodistribution of LHbisD4 in tumor tissues was performed in a separate group of SCC7-tumor-bearing mice (n=3-4 for each time point) by a method described previously. For all bio-distribution studies, we used a fluorescent marker for tracking LHbisD4. Mice were administered LHbisD4-Cy5.5 by oral gavage (10 mg/kg). Mice were perfused with PBS buffer (30 mL) at pre-designated time points (0.5, 2, 4, 8 and 24 hours). The fluorescent Cy5.5 was extracted from the tissues by incubation with formamide for 48 hours at 25° C. Samples were centrifuged, and the signal intensity of fluorescence of supernatants was detected with a Wallac 1420 VICTOR plate-reader (Perkin-Elmer Life Sciences) with excitation/emission at 670 nm/720 nm. The results were normalized to protein levels in the corresponding tissues. Tissue autofluorescence was corrected by subtracting the fluorescent signal of the non-treated tumors from the respective readings in the treated mice. The amount of LHbisD4 was calculated as per gram of tissue. Similarly, the levels of fluorescent signal in mouse sera were measured at different time points (15 minutes, 30 minutes, 1, 2, 3, 4, 6, 8, 10 and 24 hours) using excitation/emission readings at 670 nm/720 nm.

Orally administered LHbisD4 showed a maximum plasma concentration of 9.3±1.4 μg/mL in rats (FIG. 9). When given orally, the targeting ability of LHbisD4 was evaluated first, in vivo, in spheroid-based angiogenesis models using TEC and $TEC^{-/-dpl}$. The fluorescence signal in the TEC plug was significantly higher than that of the

Figure 10:
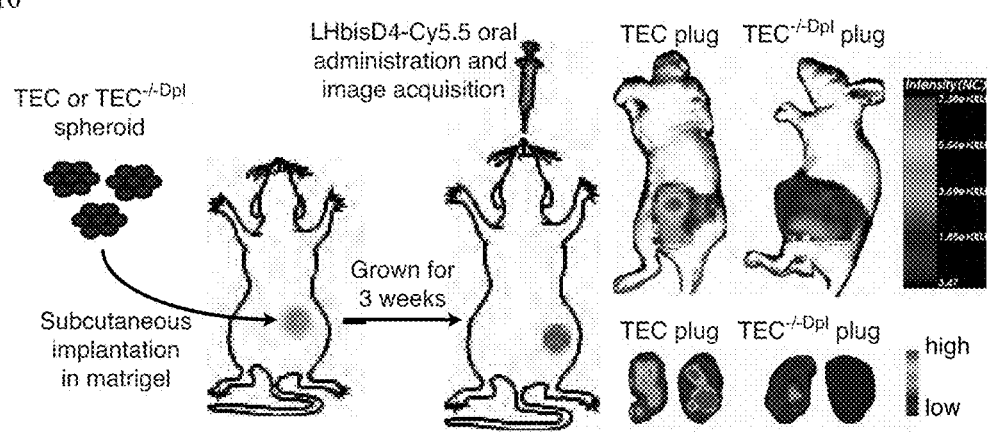
FIG. 10 Distribution of Cy5.5-labeled LHbisD4 in TEC and TEC$^{-/-dpl}$ plug, both in vivo and ex vivo after its oral delivery.
Figure 11:
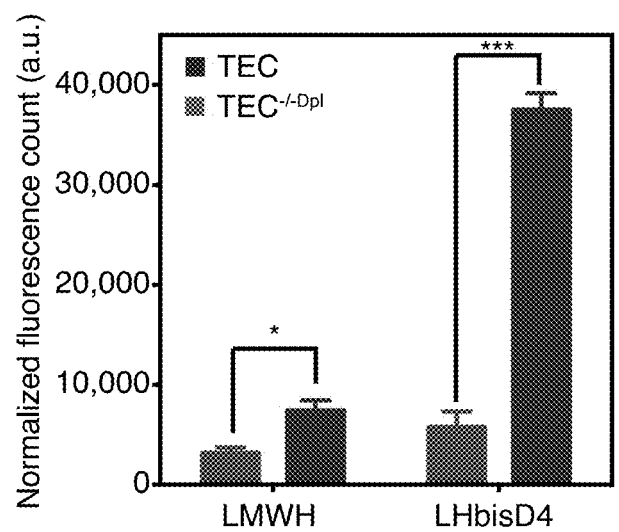
FIG. 11 is the total fluorescence count of orally administered LHbisD4 and intravenously injected LMWH in TEC and TEC$^{-/-dpl}$ plug (mean±s.e.m.).

TEC$^{-/-dpl}$ plug for orally administered Cy5.5-labeled LHbisD4 (TEC/TEC$^{-/-dpl}$ ratio 6.5±0.8 fold, p<0.001; FIGS. 10 and 11).

Example 8: Inhibition of Doppel for Treating a Tumor

This example illustrates methods of treating tumors by inhibiting pathological angiogenesis by targeting doppel and the doppel-VEGFR2 axis.

SCC7 (1×10$^6$ cells) cells were subcutaneously inoculated at the dorsal flank of C3H/HeN mice (male, 6-7 weeks old, n=6-8, Orient Bio Inc., Seongnam, Korea). When tumors reached 50-70 mm$^3$, mice were treated orally with LHbisD4 (10 mg/kg) daily for three weeks. Mice were sacrificed when tumors reached a volume greater than 2.5 cm$^3$.

MDA-MB-231 cells were injected into Balb/c nude mice (male, 6-7 weeks old, n=6-8, Orient Bio Inc., Seongnam, Korea). LHbisD4 (2.5, 5, and 10 mg/kg) was administered every day by oral gavage.

For another group of mice, LHbisD4 was administered twice daily at doses of 5 and 10 mg/kg. Mice were sacrificed when tumors reached a volume greater than 1.8 cm$^3$.

For another group of mice, anti-doppel antibody was administered once per 4 days at a dose of 1 mg/kg. Mice were sacrificed when tumors reached a volume greater than 3.0 cm$^3$.

Figure 12:
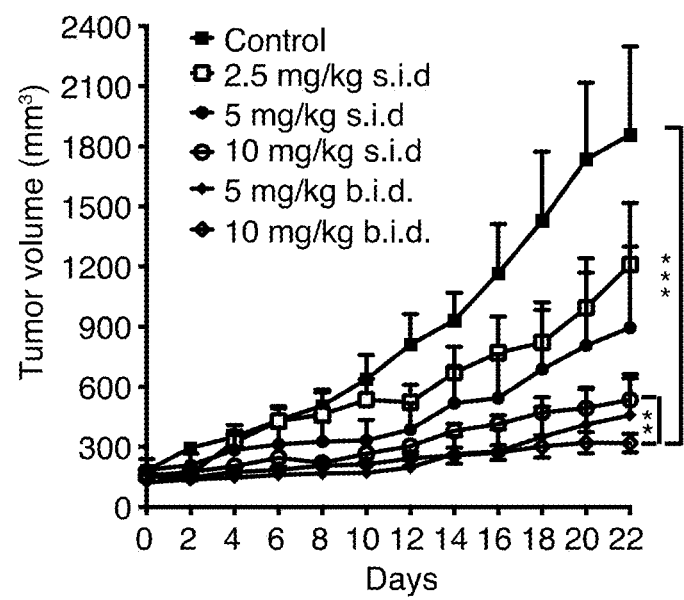
FIG. 12 shows the tumor growth inhibition study of orally administered LHbisD4 in MDA-MB-231 tumor at doses of 2.5, 5, and 10 mg/kg once daily or 5 and 10 mg/kg twice daily. Results are mean±s.e.m. * p<0.001 between each of the groups and control group.  p<0.01 between 10 mg/kg once daily and 10 mg/kg twice daily group.
Figure 13:
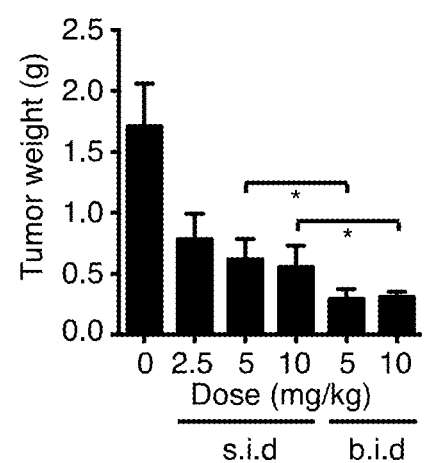
FIG. 13 shows the differences in MDA-MB-231 tumor weight when treated with different doses of LHbisD4 studied (mean±s.e.m., * p<0.05).

The antitumor effect of LHbisD4 was also observed in MDAMB-231 human breast carcinoma xenograft models (FIGS. 12 and 13). The result indicated that LHbisD4 showed a dose-dependent effect up to 10 mg/kg; that is, tumor growth was inhibited to a greater extent when the dose of LHbisD4 was increased.

Figure 14:
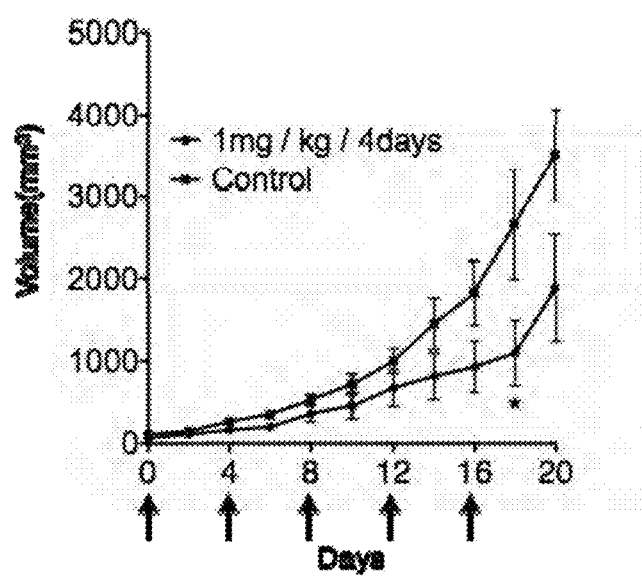
FIG. 14 shows the tumor growth inhibition study in SCC7 tumor of intravenously injected anti-doppel antibody at a dose 1 mg/kg once per 4 days. Results are mean±s.e.m.

The antitumor effect of anti-doppel antibody was also observed in SCC7 xenograft models and tumor volume was significantly decreased compared to control groups (FIG. 14). These results highlight the success of doppel targeting, in achieving selective angiogenesis inhibition.

Figures 15A, 15B, 15C, 15D:
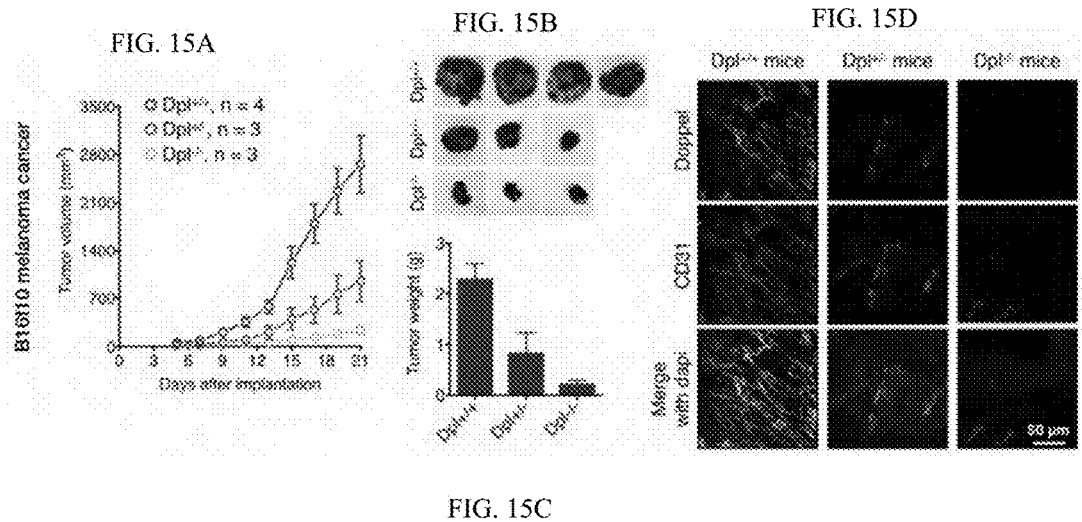
FIGS. 15A-15D show that absence of doppel in mice delays tumor growth and angiogenesis of melanoma (B16f10) in wild type (WT), and doppel heterozygous (Dpl$^{+/-}$), and homozygous (Dpl$^{-/-}$) knockout C57BL/6 mice (n=3-4). Tumor volume was monitored for 21 days after inoculation (FIG. 15A). Photographs of tumors isolated at the end of experiments are shown (FIG. 15B). The average tumor weight also was assessed (FIG. 15C). The data are in mean±s.e.m.; * P<0.001 versus WT and P<0.01 between Dpl$^{+/-}$ and Dpl$^{-/-}$.

Example 9: Development of an Anti-Doppel mAb Selectively Arrests Tumor Angiogenesis, and Eliminates the Off-Tumor Effects of Anti-Angiogenic Therapy A complete doppel knockout (KO) mouse model from immunogenic C57BL/6 mice was created (see Behrens A, Brandner S, Genoud N, Aguzzi A. Normal neurogenesis and scrapie pathogenesis in neural grafts lacking the prion protein homologue Doppel. EMBO Rep. 2001; 2:347-352). The influence of doppel deletion on tumor growth in mice was studied. Wild-type (WT), heterozygous (Dpl$^{+/-}$) and homozygous (Dpl$^{-/-}$) doppel KO mice of both sexes were born and grew without any developmental problems, suggesting that absence of doppel does not produce any congenital damage. Syngeneic B16F10 melanoma, EL4 thymoma, and CT26 colon cancer cells were innoculated into WT, Dpl$^{+/-}$, and Dpl$^{-/-}$ KO littermates (n=3-4), measured tumors for 3 weeks after inoculation, and calculated tumor volumes. Tumor volume and mass were significantly smaller in doppel KO mice compared with WT littermates (FIG. 15 A-C and FIG. 16 A-C and FIG. 17 A-C). A gene dosage effect was also observed in tumor development: heterozygous Dpl$^{+/-}$ mice had slightly larger tumors than homozygous Dpl$^{-/-}$ mice. Whole-mount immunofluorescence (IF) staining revealed that tumors in WT mice had extensive vascular beds, but tumors in Dpl$^{+/-}$ and Dpl$^{-/-}$ KO mice had fewer vessels with a sparse vascular network (FIG. 15D and FIG. 16D and FIG. 17D). No doppel was expressed in tumor vessels of Dpl$^{-/-}$ KO mice; Dpl$^{+/-}$ KO mice showed fewer doppel-positive tumor vessels than WT did. However, doppel deletion in mice did not interfere with the healing rate of body's normal wounds, which involve physiological angiogenesis (FIG. 18A, B). A 6-mm-diameter wound was created in the opposite flank of tumor-bearing doppel WT and KO mice. The wound healing rates in Dpl$^{+/-}$ and Dpl$^{-/-}$ KO mice were no different than those in WT littermates. The density of the vasculatures in the healing wound tissue of WT mice was the same as that in KO mice. Matrigel-induced vascularization was also normal in WT and KO mice (FIG. 18C, D). CD31-staining showed equal vascular networks and hemoglobin content in the matrigel plugs explanted from WT and KO mice. Thus, absence of doppel slows tumor growth in mice without interfering with physiological angiogenesis.

Custom made murine anti-doppel mAbs were acquired and tested for recognition of mouse doppel present in host-derived blood vessels of tumors, ability to block doppel function in vitro, and ability to arrest tumor growth. The selection strategy involved screening for binding with mouse doppel using ELISA and testing for ability to detect doppel protein in TEC lysates using western blot. Six independent clones (7D9, 1B12, 1C8, 5C7, 4D6, and 6F11) were identified. Of the six clones, 5C7 and 4D6 abrogated mouse VEGF (mVEGF)-induced sprouting of TEC spheroids (FIG. 20A, B). The two most potent clones (5C7 and 4D6), were purified by protein A affinity chromatography, and tested for their inhibitory effect on doppel/VEGFR2 signaling. Purified 5C7 and 4D6 clones dose-dependently prevented mVEGF-induced VEGFR2 phosphorylation in TECs and sprouting of TEC spheroids (FIG. 20C, D).

These initial studies demonstrate that anti-doppel mAb clones antagonize doppel-mediated angiogenic activity.

Based on the in vitro data, we selected clone 4D6 and 5C7 to study the anti-tumor and anti-angiogenic effect of in a murine-derived CT26 colon cancer model. When the tumors reached an average size of 50 mm$^3$, we treated the mice with intravenous doses of 5 and 10 mg/kg 4D6 and 5C7 mAb clones. 5C7 and 4D6 mAbs markedly regressed both tumor volume and weight compared to saline and control IgG treated groups; 4D6 showed superior activity (FIG. 19A, B and FIG. 21A). When administered at a dose of 10 mg/kg once or twice a week, 4D6 mAb reduced the tumor growth by 71.1±4.2% or 87.9±3.9%, respectively. In mAb-treated tumors, the numbers of doppel-(red) and CD31-positive vessels (green) were significantly lower compared to the saline- or IgG-treated tumors (FIG. 21B); mean vessel density also decreased along with tumor volume (FIG. 21C).

Preliminary studies with 4D6 and 5C7-treated tumor-bearing mice showed no changes in body weight, no obvious organ pathology upon inspection and histological analysis, and no alteration in the clinical chemistry or hematological blood profile.

The antitumor effect of 4D6 mAb was also observed in HCT116 human colon cancer mouse xenografts. 4D6 mAb inhibited tumor growth (FIG. 19C, D), doppel- and CD31-positive tumor vessels (FIG. 19E), and mean tumor blood vessels density commensurately with dose and dosing frequency (FIG. 19F, G).

In summary, anti-doppel mAb treatment, in a therapeutic context, limits tumor progression.

Figure 23A:
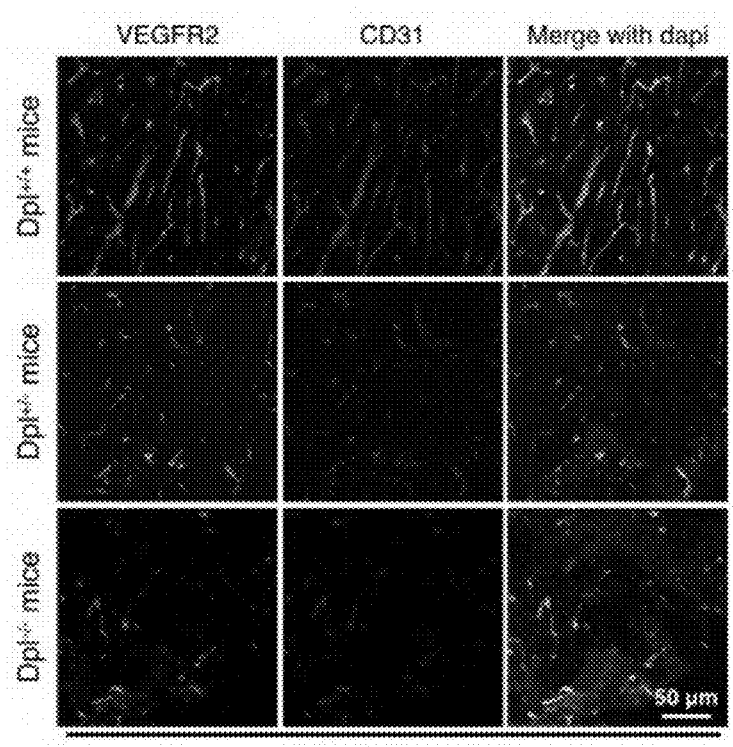
FIGS. 23A-23B show immunofluorescent images of VEGFR2 (green), CD31 (red), and DAPI (blue) in EL4 tumor sections isolated from WT, $Dpl^{+/-}$, and $Dpl^{-/-}$ mice (FIG. 23A) and in CT26 tumor sections isolated from WT and $Dpl^{+/-}$ mice (FIG. 23B).
Figure 23B:
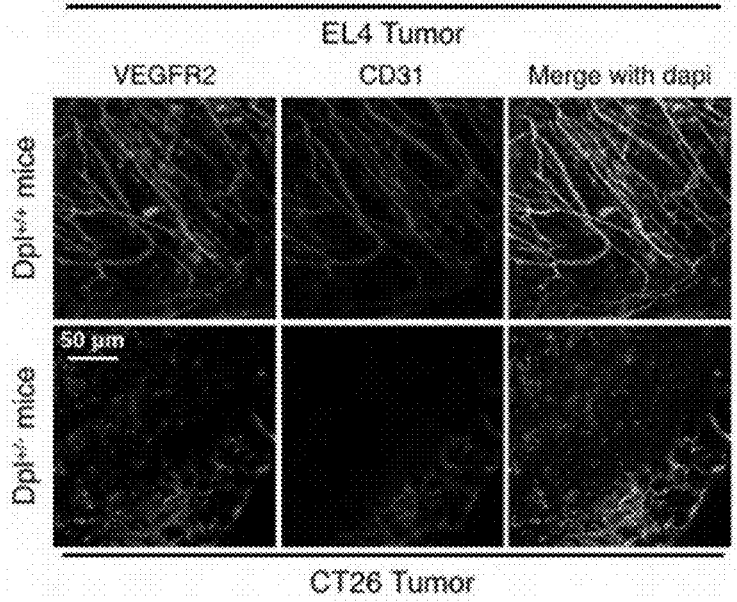
Figure 24A:
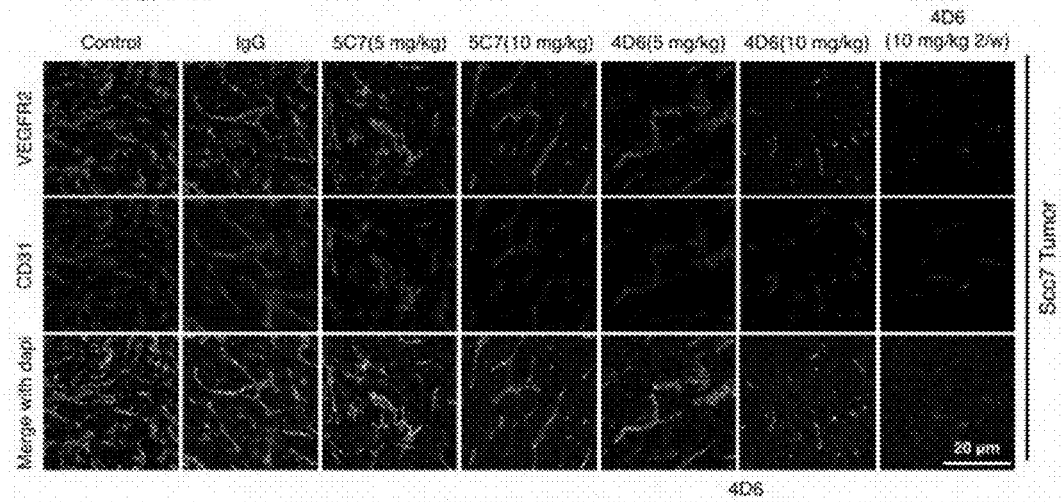
FIGS. 24A-24B show immunofluorescent images of VEGFR2 (green), CD31 (red), and DAPI (blue) in mouse CT26 colon cancer (FIG. 24A) and human HCT116 colon tumor sections (FIG. 24B) isolated from mice treated with saline and test antibodies.
Figure 24B:
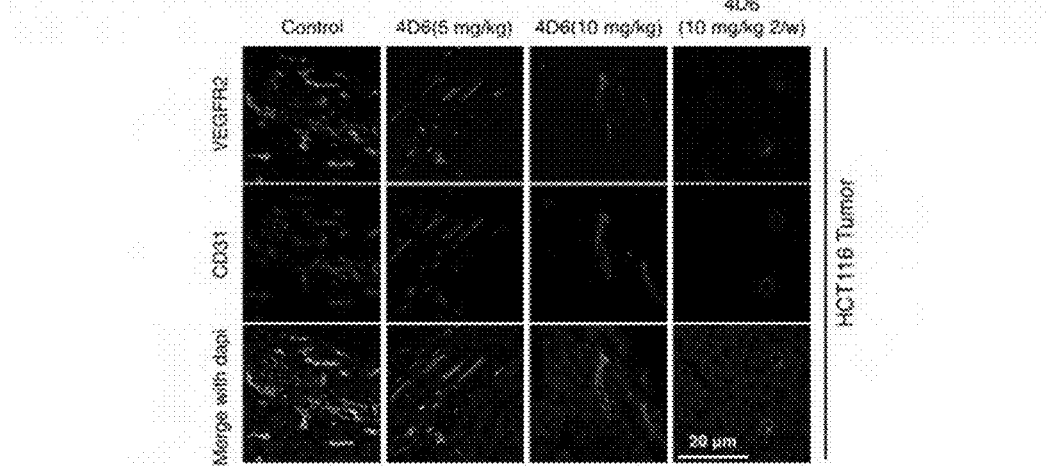

The influence of doppel on angiogenesis and VEGF2 expression was studied by visualizing the vascular networks and measuring VEGFR2 levels in explanted tumors and normal lungs from WT, Dpl$^{+/-}$ and Dpl$^{-/-}$ KO mice and 4D6 anti-dopple mAb treated mice. Genetic deletion of doppel reduced VEGFR2 expression in tumors in Dpl$^{+/-}$ and Dpl$^{-/-}$ KO mice compared with WT mice; however, VEGFR2 expression was not changed in the lungs of tumor-bearing mice (FIG. 22A, B and FIG. 23 and FIG. 24).

Figures 25A, 25B, 25C:
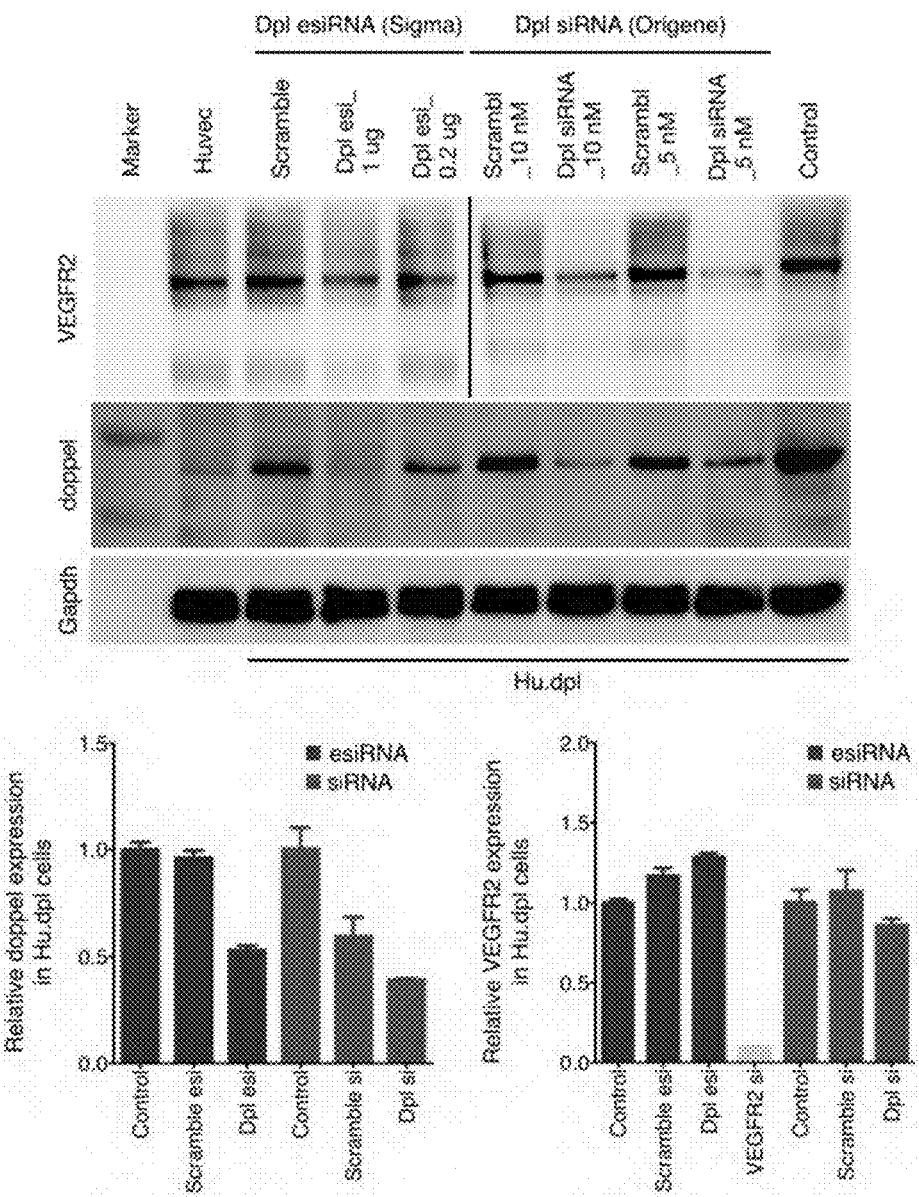
FIG. 25A show inhibition of doppel expression by doppel siRNA in doppel transfected HUVEC (Hu.dpl).
FIG. 25B and FIG. 25C show mRNA levels of doppel (FIG. 25B) and VEGFR2 (FIG. 25C) following treatment with scramble and doppel esiRNA or siRNA in Hu.dpl.

To investigate doppel's roles in VEGFR2 signaling, the doppel gene was silenced in two different TECs isolated from squamous cancer (TEC-SCC7) and colon cancer (TEC-CT26) and doppel-transfected HUVECs (Hu.dpl) using doppel siRNAs; cells transfected with scrambled siRNA were used as controls. Doppel silencing decreased the protein level of both doppel and VEGFR2 in TEC-SCC7, TEC-CT26 (FIG. 22C) and in Hu.dpl (FIG. 25A). In contrary, doppel silencing decreased the mRNA level of doppel (FIG. 22D and FIG. 25B), but did not change VEGFR2 mRNA level in those cells (FIG. 22E and FIG. 25C). Based on the observation that the protein level, but not mRNA level, of VEGFR2 changed in doppel-silenced ECs, it was hypothesized that doppel extends and stabilizes the cell surface retention of VEGFR2 and makes it more responsive to VEGF.

Figures 26A, 26B, 26C:
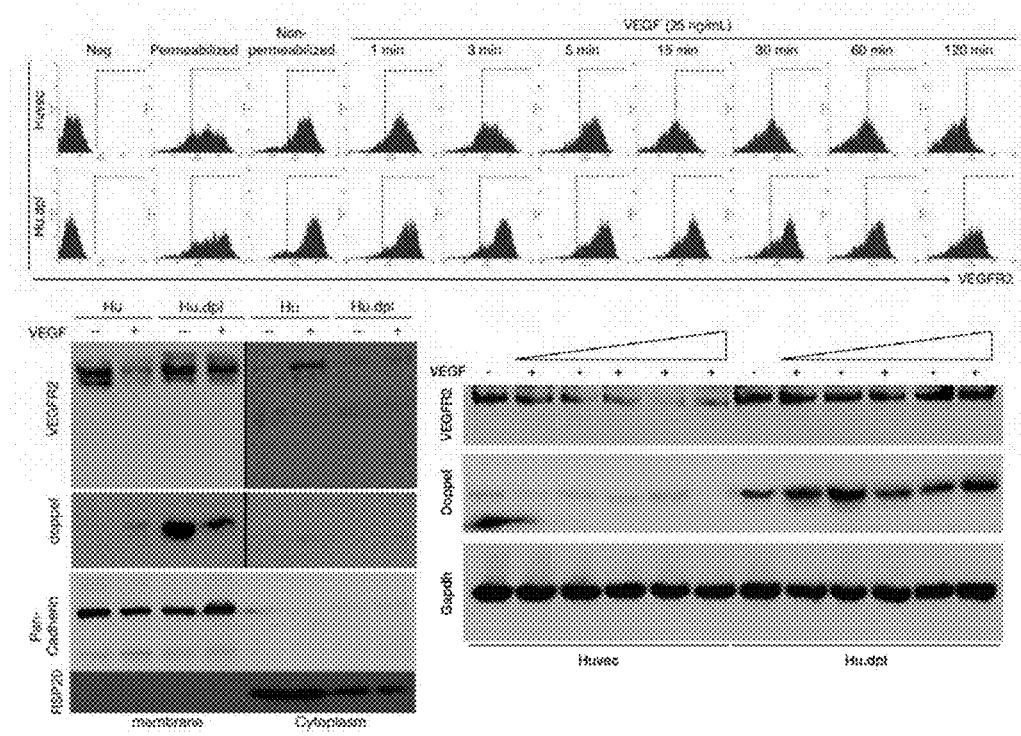
FIGS. 26A-26C show the flow cytometry analysis of VEGFR2 after incubation with VEGF (25 ng/mL) in non-permeabilized HUVECs and Hu.dpl (FIG. 26A); blots representing the membrane and cytoplasmic VEGFR2 and doppel levels in unstimulated and VEGF-stimulated (5 minutes; 100 ng/mL) HUVECs and Hu.dpl (FIG. 26B); and blots representing the total VEGFR2 and doppel levels in unstimulated and different concentrations of VEGF-stimulated (5 minutes) HUVECs and Hu.dpl (FIG. 26C).
Figure 29A:
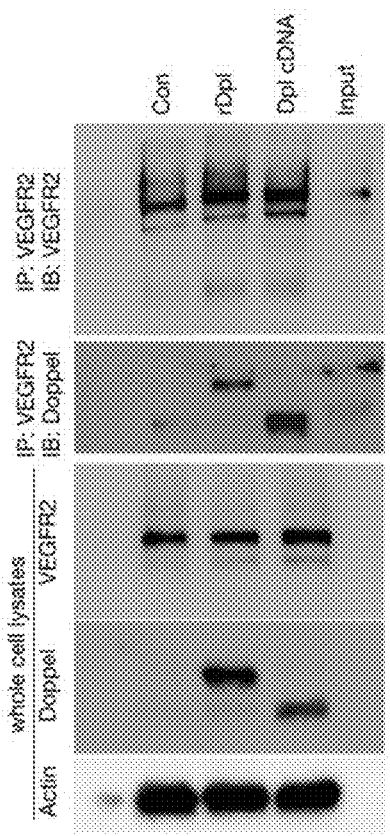
FIGS. 29A-29B show that doppel interacts with VEGFR2.
Figure 29B:
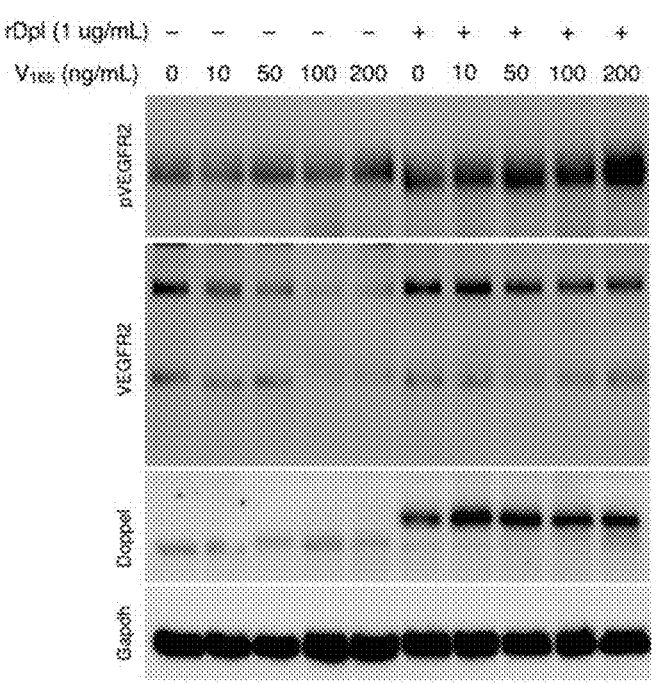

VEGF triggers VEGFR2 internalization and rearranges the signaling clusters on the EC surface. Thus, the membrane distribution of VEGFR2 in HUVECs and Hu.dpl cells was evaluated by stimulating the cells with VEGF. The surface receptors of the cells were labeled with sulfo-NHS-biotin, lysed the cells, precipitated the lysates with streptavidin-conjugated magnetic beads, and analyzed the precipitates by immunoblot with anti-VEGFR2 and anti-doppel antibodies. VEGF-stimulated HUVECs internalized more VEGFR2 than VEGF-stimulated Hu.dpl cells did (FIG. 22F); receptor internalization was proportional to surface doppel amount. HUVECs internalized VEGFR2, determined by FACS analysis, at a faster rate than Hu.dpl cells did due to VEGF stimulation (FIG. 22G and FIG. 26A). Short exposure of VEGF depleted VEGFR2 from the membrane and increased the intracellular pool of the receptor in HUVECs; however, the membrane content of VEGFR2 was similar in Hu.dpl in the presence or absence of VEGF (FIG. 26B). Total VEGFR2 was unaltered in Hu.dpl by the increasing concentrations of VEGF (FIG. 26C).

The effect of doppel on VEGFR2 dimerization in the absence of VEGF was investigated. In situ proximity ligation assay (PLA) was used to see VEGFR2 homodimers/clusters in intact cells (FIG. 22G, H). Hu.dpl cells had higher VEGFR2 homodimers than HUVECs did; VEGFR2 dimerization/clustering was severely compromised after doppel siRNA or 5C7 anti-doppel mAb treatment (FIG. 22G, H). It was observed that the dynamics between VEGFR2 monomer-dimer using western blot (FIG. 28A). In HUVECs, the prominent 125 kDa and a relative weaker 250 kDa band appeared as VEGFR2 monomer and dimer, respectively. In Hu.dpl cells, VEGFR2 was detected at 250 kDa band in immunoblots. However, in Hu.dpl cells treated with doppel siRNA or 5C7 anti-doppel mAb the band appeared at 125 kDa (FIG. 28B), suggesting that VEGFR2 favors dimerization/clustering in the presence of doppel.

Correspondingly, the same VEGF concentrations dose dependently reduced the total level of VEGFR2 in HUVECs. The phosphorylation of VEGFR2 in Hu.dpl cells was greater than that in HUVECs, when stimulated with increasing concentrations of VEGF (FIG. 28C). Thus, doppel controls VEGFR2 distribution, maintains a high level of VEGFR2 on the cell surface, and expedites and sustains VEGFR2 signaling. Overall, the data elucidate that doppel functions by modulating VEGFR2 signaling.

The role of doppel in tumor angiogenesis was evaluated in a rescue model involving either re-expressing doppel using cDNA transfection or treating with recombinant doppel (rDPl) protein. Human dermal microvascular endothelial cells (HDMEC) were transfected for these studies. VEGF-mediated VEGFR2 phosphorylation, proliferation of the cells, and sprouting of HDMEC spheroids greatly increased in doppel cDNA-transfected cells as compared to mock or control cells (FIG. 29A-D). Co-immunoprecipitation experiments using both doppel cDNA-transfected and rDPl-treated cells showed physical interactions between VEGFR2 and doppel or VEGFR2 and rDPl (FIG. 30A). In the presence of rDPl, VEGF robustly and dose dependently increased VEGFR2 phosphorylation (FIG. 30B). A similar phenomenon was observed for doppel transfected HDMECs and Hu.dpl. These in-vitro studies indicate that soluble rDPl act as membrane bound doppel and helps to induce angiogenesis.

To test this hypothesis, HUVEC spheroids were treated with VEGF in the presence or absence of rDPl. VEGF promoted HUVEC spheroid sprouting; the sprouting was augmented when co-treated with different concentrations rDPl and in Hu.dpl spheroids (FIG. 27A).

HUVEC spheroids in vivo were implanted in Matrigel-fibrin gel in the presence of doppel and VEGF following an established protocol (see Alajati et al., Nat Methods. 5:439-445 (2008) and Laib et al., Nat Protoc. 4:1202-1215 (2009)); Hu.dpl spheroids were used to compare. HUVEC spheroids failed to grow any vascular network after 1 week of implantation in the absence of VEGF and rDPl; presence of VEGF stimulated the vessel formation (FIG. 27B). In contrast, the presence of VEGF and rDPl generated a complete and perfused vascular bed in the Matrigel-fibrin gel. The hemoglobin content of VEGF and rDPl-treated HUVEC spheroids, an indicator of perfused vessels, was higher than control and VEGF-treated spheroids and similar to those Hu.dpl spheroids (FIG. 27C). These findings support that rDPl enhances angiogenesis in tumor.

To rescue angiogenesis and growth of tumor, Dpl$^{+/-}$ KO mice were treated with intravenous injection of 1 mg/kg of rDPl three times after the 4$^{th}$ day of EL4 tumor inoculation. EL4 cells were also inoculated with 1 and 10 µg of rDPl in a mixture with 50 µL of Matrigel, in Dpl$^{+/-}$ KO mice and grown for 10 days. The rDPl mixture dose dependently rescued the growth of tumors in Dpl$^{+/-}$ KO mice; the tumor size and weight was similar between 10 µg of rDPl-mixed and WT control littermates or 1 µg of rDPl-mixed and intravenous rDPl-treated mice (FIG. 27D-F). In tumor tissues, intravenously injected rDPl concentrated and colocalized with VEGFR2- and CD31-positive vessels (FIG. 31). These data demonstrate that the pro-angiogenic effect of doppel is apparent in vivo and corresponds with improved tumor growth.

Most regulators that control the spatial distribution of tyrosine kinase receptors are equally important for both developmental and tumor angiogenesis, metastasis or resistance mechanisms against the therapeutic response. This study identifies doppel-VEGFR2 interactions as a key driver of VEGFR2 trafficking and signaling for selective control of tumor angiogenesis. While not wanting to be bound by theory, we believe that doppel tilts the angiogenic balance toward the 'on' mode, prolongs cell-surface retention of VEGFR2, and helps to continue VEGF-signaling. Genetic erasure and pharmacological inhibition of doppel limits VEGF/VEGFR2-signaling in tumors, reduces VEGFR2 expression in TECs, slows tumor vessels growth, and shrink tumors, but preserves VEGF-functionality in normal tissues.

These data strongly support a central assumption that doppel is a pro-angiogenic factor and that doppel-targeting molecules such as anti-doppel mAb are viable anti-angiogenic agents. Again, while not being bound by theory, it is believed that doppel-targeting molecules, including the novel anti-doppel mAb described herein, block doppel, which has no known role in normal (non-pathological) physiological angiogenesis.

What is claimed is:

1. A method of inhibiting pathological angiogenesis in a subject in need thereof, comprising administering to the subject an effective amount of a doppel-targeting molecule that binds to doppel and inhibits doppel-tyrosine kinase receptor signaling, selected from:
   (i) an antibody produced by hybridoma cell line clone 4D6;
   (ii) an antibody produced by hybridoma cell line clone 5C7;
   (iii) an antibody produced by hybridoma cell line clone 7D9;
   (iv) an antibody produced by hybridoma cell line clone 1B12;
   (v) an antibody produced by hybridoma cell line clone 1C8; and
   (vi) an antibody produced by hybridoma cell line clone 6F11.

2. The method of claim 1, wherein the effective amount is effective to interfere with the interaction of doppel and the tyrosine kinase receptor VEGFR2.

3. The method of claim 1, wherein the effective amount is effective to inhibit angiogenesis.

4. The method of claim 1, wherein the doppel-targeting molecule is administered by oral administration, subcutaneous injection, intravenous injection, intraocular injection, intradermal injection, intramuscular injection, intraperitoneal injection, intratracheal administration, inhalation, intranasal administration, sublingual administration, buccal administration, rectal administration, vaginal administration, or topical administration.

5. The method of claim 1, wherein the subject suffers from or is at risk of developing a tumor, and the effective amount is effective to inhibit tumorigenesis and/or to decrease tumor vasculature.

6. The method of claim 1, wherein the subject suffers from or is at risk of developing a disease or condition selected from cancer, atherosclerosis, tuberculosis, asthma, pulmonary arterial hypertension (PAH), a neoplasm or neoplasm-related condition, and the effective amount is effective to decrease pathological vasculature associated with the cancer, atherosclerosis, tuberculosis, asthma, pulmonary arterial hypertension (PAH), a neoplasm or neoplasm-related condition, respectively.

7. The method of claim 6, wherein the neoplasm or neoplasm-related condition is selected from breast carcinoma, lung carcinoma, gastric carcinoma, esophageal carcinoma, colorectal carcinoma, liver carcinoma, ovarian carcinoma, arrhenoblastoma, cervical carcinoma, endometrial carcinoma, endometrial hyperplasia, endometriosis, fibrosarcoma, choriocarcinoma, head and neck cancer, nasopharyngeal carcinoma, laryngeal carcinoma, hepatoblastoma, Kaposi's sarcoma, melanoma, skin carcinoma, hemangioma, cavernous hemangioma, hemangioblastoma, pancreas carcinoma, retinoblastoma, astrocytoma, glioblastoma, Schwannoma, oligodendroglioma, medulloblastoma, neuroblastoma, rhabdomyosarcoma, osteogenic sarcoma, leiomyosarcoma, urinary tract carcinoma, thyroid carcinoma, Wilm's tumor, renal cell carcinoma, prostate carcinoma, abnormal vascular proliferation associated with phakomatoses, edema associated with a brain tumor, and Meigs' syndrome.

8. The method of claim 1, wherein the subject is a human.

9. The method of claim 1, wherein the doppel-targeting molecule is an antibody produced by hybridoma cell line clone 4D6.

10. The method of claim 1, wherein the doppel-targeting molecule is an antibody produced by hybridoma cell line clone 5C7.

11. The method of claim 1, wherein the doppel-targeting molecule is an antibody produced by hybridoma cell line clone 7D9.

12. The method of claim 1, wherein the doppel-targeting molecule is an antibody produced by hybridoma cell line clone 1B12.

13. The method of claim 1, wherein the doppel-targeting molecule is an antibody produced by hybridoma cell line clone 1C8.

14. The method of claim 1, wherein the doppel-targeting molecule is an antibody produced by hybridoma cell line clone 6F11.

* * * * *

```
                               SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggacatcgac tttggagcag ag                                               22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagcatctcc ttggtcacgt tg                                               22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gatggcatcc actacaacgg ct                                               22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gttgtctggc ttctggaact cc                                               22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gccttcaaga ctctgttcgt gg                                               22

<210> SEQ ID NO 6
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 6
ctcgatgaag gcataaccac gg                                              22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcaagactct cttcgtggcg ag                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggctttcctg accgcttact gt                                              22
```